(12) United States Patent
Uchiyama et al.

(10) Patent No.: US 8,335,556 B2
(45) Date of Patent: Dec. 18, 2012

(54) MAGNETICALLY DRIVEN CAPSULE MEDICAL DEVICE AND CAPSULE MEDICAL DEVICE SYSTEM WITH POSITION DETECTION

(75) Inventors: Akio Uchiyama, Kanagawa (JP); Atsushi Kimura, Tokyo (JP); Ryoji Sato, Tokyo (JP); Atsushi Chiba, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 923 days.

(21) Appl. No.: 12/304,917

(22) PCT Filed: Jun. 27, 2007

(86) PCT No.: PCT/JP2007/062909
§ 371 (c)(1),
(2), (4) Date: Dec. 15, 2008

(87) PCT Pub. No.: WO2008/001810
PCT Pub. Date: Jan. 3, 2008

(65) Prior Publication Data
US 2009/0326323 A1    Dec. 31, 2009

(30) Foreign Application Priority Data

Jun. 29, 2006  (JP) ................................. 2006-179336
Jul. 3, 2006   (JP) ................................. 2006-183424

(51) Int. Cl.
*A61B 5/00*   (2006.01)
(52) U.S. Cl. ...................................................... 600/424
(58) Field of Classification Search .................. None
See application file for complete search history.

(56) References Cited

U.S. PATENT DOCUMENTS

| | | | | |
|---|---|---|---|---|
| 5,253,647 | A | * | 10/1993 | Takahashi et al. ............ 600/424 |
| 5,681,260 | A | * | 10/1997 | Ueda et al. ..................... 600/114 |
| 5,729,129 | A | * | 3/1998  | Acker ....................... 324/207.12 |

(Continued)

FOREIGN PATENT DOCUMENTS

EP    1 504 713 A1    2/2005

(Continued)

OTHER PUBLICATIONS

Extended Supplementary European Search Report dated Feb. 12, 2010.

(Continued)

*Primary Examiner* — Jacqueline Cheng
(74) *Attorney, Agent, or Firm* — Scully, Scott, Murphy & Presser, P.C.

(57) ABSTRACT

Smooth guiding through the inside of a body cavity is carried out by a magnetic field applied from the outside of the body. The provided capsule medical device (1) includes a bio-information detecting device (5) for detecting bio information of the inside of a body cavity; a magnet (12) for receiving a guidance magnetic field applied from outside the body and generating a driving force; a coil (7) for receiving a position-detection magnetic field applied from outside the body and generating a position-detection signal; a filter device (8), connected to the coil (7), for attenuating an induction signal component which is generated by the guidance magnetic field incident on the coil (7); and a wireless transmission device (10) for externally transmitting the position-detection signal which has passed through the filter device (8) and the bio information which has been detected by the bio-information detecting device (5).

33 Claims, 18 Drawing Sheets

U.S. PATENT DOCUMENTS

| | | | |
|---|---|---|---|
| 6,233,476 B1 * | 5/2001 | Strommer et al. | 600/424 |
| 6,833,814 B2 * | 12/2004 | Gilboa et al. | 342/448 |
| 7,706,859 B2 * | 4/2010 | Aizawa et al. | 600/424 |
| 2005/0049461 A1 * | 3/2005 | Honda et al. | 600/160 |
| 2005/0187479 A1 | 8/2005 | Graumann | |
| 2005/0216231 A1 | 9/2005 | Aoki et al. | |
| 2006/0004253 A1 | 1/2006 | Shigemori et al. | |
| 2006/0209185 A1 * | 9/2006 | Yokoi | 348/65 |

FOREIGN PATENT DOCUMENTS

| | | |
|---|---|---|
| EP | 1 723 898 A1 | 11/2006 |
| JP | 2005-245963 | 9/2005 |
| JP | 2005-304511 | 11/2005 |
| JP | 2005-334081 | 12/2005 |
| JP | 2006-075536 | 3/2006 |
| JP | 2006-075537 | 3/2006 |
| JP | 2006-078295 | 3/2006 |
| WO | WO 2005/112733 A1 | 12/2005 |
| WO | WO 2005/120345 A2 | 12/2005 |
| WO | WO 2006/025400 A1 | 3/2006 |

OTHER PUBLICATIONS

Date-of-Receipt letter to establish the date (Mar. 1, 2010) on which the European Search Report was received.

Extended European Search Report dated Feb. 16, 2011.

* cited by examiner

MAGNETICALLY DRIVEN CAPSULE MEDICAL DEVICE AND CAPSULE MEDICAL DEVICE SYSTEM WITH POSITION DETECTION

TECHNICAL FIELD

The present invention relates to a capsule medical device inserted into a body cavity and a capsule medical device system.

The present invention relates to a capsule medical device system including a capsule medical device that is introduced into a body of a subject and moves inside the subject and a position detection device that detects the position of the capsule medical device inside the subject using a position-detection magnetic field having a position dependent intensity.

BACKGROUND ART

There is a known capsule medical device system that has a magnet inside a capsule medical device and that controls the position and orientation of the capsule medical device by applying a magnetic field from the outside (for example, refer to Patent Document 1).

With the capsule medical device system according to Patent Document 1, a spiral-propulsion generating mechanism is provided on the outer circumferential surface of a capsule endoscope, and the capsule medical device is propelled by applying a rotating magnetic field from the outside to the internal magnet.

With this capsule medical device system, a magnetic field for position detection is generated outside the body, and an induced magnetic field generated at a magnetic induction coil disposed inside the capsule medical device is detected outside the body. In this way, the current position and orientation of the capsule medical device inside a body cavity can be detected. Consequently, the capsule medical device can be smoothly guided inside the body cavity.

Recently, in the field of endoscopes, a capsule endoscope system (capsule medical device system) using a swallowable capsule endoscope (capsule medical device) has been proposed. Such a capsule endoscope includes an image-acquisition mechanism and a wireless communication mechanism. A capsule endoscope that can be moved through the inside of internal organs, such as the stomach and the small intestine, by applying a magnetic force from the outside after it is introduced into a body cavity through the mouth etc. of the subject for observation (examination) has been proposed. In this way, images of desired sites in the body cavity can be captured. While the capsule endoscope moves through the body cavity of the subject, the image data of the inside of the body cavity captured by the capsule endoscope is sequentially transmitted to the outside by wireless communication and is stored in an externally provided memory or is displayed as images on an externally provided display.

Among capsule endoscope system in the related art, one provided with a mechanism for detecting the position of a capsule endoscope inside a body cavity has been proposed. For example, Patent Document 2 describes a capsule endoscope system that introduces, inside a subject, a capsule endoscope that generates a magnetic field having a position dependent intensity and detects the position of the capsule endoscope inside the subject on the basis of the intensity of the magnetic field detected by a magnetic sensor mounted inside the capsule endoscope.

The capsule endoscope system has a configuration in which a predetermined coil is disposed outside the subject so as to generate a magnetic field. By applying a predetermined electric current to the coil, a magnetic field is generated inside the subject. In this system, for example, image data can be acquired, and at the same time, the position where the image data is acquired can be detected. Thus, the capsule endoscope system is advantageous in that the correspondence between the image data and the position in the subject is easy to grasp when diagnosis is carried out by doctor or the like.

Patent Document 1: Japanese Unexamined Patent Application, Publication No. 2005-245963
Patent Document 2: Japanese Unexamined Patent Application, Publication No. 2006-75537
Patent Document 3: Japanese Unexamined Patent Application, Publication No. 2006-78295

DISCLOSURE OF INVENTION

However, with such a capsule medical device system, since guidance of the capsule and position detection of the capsule is performed by applying a magnetic field from outside the body, not only the magnetic field for position detection but also a rotating magnetic field for guidance of the capsule medical device acts upon the magnetic induction coil inside the capsule medical device. Therefore, there is a possibility that the position and orientation of the capsule medical device cannot be detected accurately. In such a case, there is a problem in that smooth guiding of the capsule medical device cannot be carried out.

When the capsule medical device is propelled while being rotated by a rotating magnetic field applied from outside the body and a spiral-propulsion generating mechanism provided on the outer circumferential surface of the capsule medical device, rotation is not smooth due to, for example, friction between the capsule medical device and the surrounding organs, and thus the direction of the magnetic pole of the magnet inside the capsule medical device and the direction of the rotating magnetic field may be misaligned. In such a case, there is a problem in that smooth guidance of the capsule medical device cannot be carried out.

With a capsule endoscope system having a position detection function, since a coil disposed outside a subject and a magnetic-field sensor mounted inside a capsule endoscope have to operate constantly, electricity consumption of the equipment outside the subject and the capsule endoscope is large.

The present invention has been conceived in light of the problems described above, and it is an object of the present invention to provide a capsule medical device that can be smoothly guided through the inside of a body cavity by applying a magnetic field from the outside of the body, as well as a capsule medical device system.

Another object of the present invention is to provide a capsule medical device and a capsule medical device system that can reduce electricity consumption while satisfactorily detecting the position of the capsule medical device.

To achieve the objects described above, the present invention provides the following solutions.

A first aspect of the present invention provides capsule medical device including a bio-information detecting device for detecting bio information of the inside of a body cavity; a magnet for generating a driving force by a guidance magnetic field applied from outside the body; a coil for receiving a position-detection magnetic field applied from outside the body and generating a position-detection signal; a filter device, connected to the coil, for attenuating an induction signal component due to the guidance magnetic field incident on the coil; and a wireless transmission device for externally transmitting the position-detection signal which has passed through the filter device and the bio information which has been detected by the bio-information detecting device.

According to the first aspect of the present invention, when the guidance magnetic field is applied from the outside of the body, a driving force is generated by the magnet inside, and the capsule medical device inside the body cavity is propelled. Moreover, since a position-detection signal is generated at the internal coil when the position-detection magnetic field is applied from the outside of the body, the position and orientation of the capsule medical device can be detected on the basis of the position-detection signal. Then, by operating the bio-information detecting device after detecting the accurate position and orientation and guiding the capsule medical device to a desired position and orientation, desired bio information of the inside of the body cavity can be detected.

In such a case, both the guidance magnetic field and the position-detection magnetic field applied from the outside of the body act on the internal coil to generate an induction signal by means of their magnetic inductances. However, since the filter device is connected to the coil, the induced signal caused by the guidance magnetic field contained in the generated induced signal is attenuated. Then, the remaining attenuated induced signal caused by the guidance magnetic field (position-detection signal due to the position-detection magnetic field) is externally transmitted together with the detected bio information by the operation of the wireless transmission device. Therefore, it is possible to receive, outside the capsule medical device, an induced signal that is less affected by the guidance magnetic field, and smooth guidance is possible by improving the detection precision of the position and orientation.

In the above-described first aspect, it is preferable that an opening direction of the coil and a direction of a magnetic field formed by the magnet at the position of the coil be substantially orthogonal.

In this way, the transmission of the magnetic field formed by the magnet through the coil is suppressed and the effect of the magnet on the position-detection signal is reduced to improve the detection precision of the position and orientation, thus enabling smooth guidance.

In the above-described configuration, two or more of the coils may be provided, and opening directions of the coils may differ.

In this way, two or more position-detection signals corresponding to the one magnetic field applied from outside the body can be acquired, and six or more position-detection signals, which are required for determining the six degrees of freedom of the capsule medical device, can be acquired.

As described above, the two or more coils may be disposed at the same position when the two or more coils are provided and when the opening directions of the coils differ.

In this way, the space for accommodating the coils is reduced, and the size of the capsule medical device can be reduced.

In the above-described first aspect, identification information required for detecting at least one of position and orientation by using the position-detection signal may be stored, and the wireless transmission device may externally transmit the identification information.

In this way, at least one of the positions and orientations of capsule medical devices of different types can be easily detected on the basis of the identification information and the position-detection signals externally transmitted via the wireless transmission device.

In the above-described configuration, two or more of the coils may be provided, and the identification information may include relative positions of the coils and relative angles of the opening directions of the coils.

Moreover, in the above-described configuration, two or more of the coils may be provided, and the identification information may include relative positions and relative angles of the coils, relative positions of the coils and the magnet, and relative angles of the opening directions of the coils and a magnetization direction of the magnet.

In this way, at least one of the position and orientation of capsule medical device can be easily detected on the basis of the relative positions of the two or more coils, the relative angles of the opening directions of the coils and/or the relative angles of the opening directions of the coils and the magnetization direction of the magnet, and the position-detection signal.

As described above, a switching device for switching connections may be provided between the two or more coils and the filter device when the two or more coils are provided and when the opening directions of the coils differ.

In this way, the number of filter devices can be reduced, and the size of the capsule medical device can be reduced.

In the above-described first aspect, a position-detection signal processing device for processing the position-detection signal, which has passed through the filter device, and inputting it to the wireless transmission device may be provided, and the position-detection signal processing device and the bio-information detecting device may be operated in synchronization.

In this way, the processing of the position-detection signal by the position-detection signal processing device can be stopped, except for when the position-detection magnetic field is applied from the outside, by synchronizing it with the detection of the bio information by the bio-information detecting device, and power consumption can be reduced.

As described above, when the switching device is provided, the switching device and the bio-information detecting device may be operated in synchronization.

A second aspect of the present invention provides a capsule medical device system including one of the above-described capsule medical devices; and an external apparatus which is disposed outside a body, wherein the external apparatus includes, a wireless reception device for receiving a signal transmitted from the wireless transmission device, a position-detection signal extracting device for extracting the position-detection signal from the signal received by the wireless reception device, a position/orientation calculating device for calculating at least one of position and orientation of the capsule medical device on the basis of the position-detection signal extracted by the position-detection signal extracting device, a guidance-magnetic-field generating device for generating a guidance magnetic field, and a position-detection-magnetic-field generating device for generating the position-detection magnetic field.

According to the second aspect, when the guidance magnetic field is applied from the outside of the body by operation of the guidance-magnetic-field generating device provided in the external apparatus, a driving force is generated by the internal magnet, and the capsule medical device inside the body cavity is propelled. Then, bio information about the inside of the body cavity is detected by the operation of the bio-information detecting device inside the capsule medical device.

When the position-detection magnetic field is applied from the outside of the body by the operation of the position-detection-magnetic-field generating device provided in the external apparatus, a position-detection signal is generated by the coil inside the capsule medical device. Then, the generated position-detection signal is transmitted outside the body together with the bio information by operating the wireless transmission device after the induction signal component, which is generated due to the action of the guidance magnetic field, is attenuated by the filter device.

The position-detection signal transmitted to the outside of the body is received by the wireless reception device provided in the external apparatus and is separated and extracted from the bio information by the position-detection signal extracting device. Then, the position-detection signal is used by the position/orientation calculating device for calculating at least one of the position and orientation of the capsule medical device. Since the induction signal component, which is generated by the guidance magnetic field and included in the position-detection signal used for calculating the position and orientation, is attenuated by the operation of the filter device, the position and orientation can be calculated with good precision, and the capsule medical device can be smoothly guided. Consequently, the capsule medical device, which is guided to a desired position and orientation, can detect desired bio information of the inside of the body cavity.

A third aspect of the present invention provides a capsule medical device system including one of the above-described capsule medical devices; an external apparatus disposed outside a body, wherein the external apparatus includes a wireless reception device for receiving a signal transmitted from the wireless transmission device, an information extracting device for extracting the position-detection signal and the identification information from the signal received by the wireless reception device, a position/orientation calculating device for calculating a position and an orientation of the capsule medical device and a magnetization direction of the magnet on the basis of the position-detection signal and the identification information extracted by the information extracting device, a guidance-magnetic-field generating device for generating a guidance magnetic field, and a position-detection-magnetic-field generating device for generating the position-detection magnetic field.

According to the third aspect, the identification information stored in the identification-information storing device of the capsule medical device is transmitted by the external apparatus via the wireless transmission device of the capsule medical device and the wireless reception device of the external apparatus. In the external apparatus, the position and orientation of the capsule medical device and the magnetization direction of the magnet are calculated with good precision by the operation of the position/orientation calculating device on the basis of the position-detection signal and identification information extracted by the information extracting device. In this way, even when the capsule medical device to be used is changed, this capsule medical device can be smoothly guided.

A fourth aspect of the present invention provides a capsule medical device system including the above-described capsule medical devices; and an external apparatus disposed outside a body, wherein the external apparatus includes a wireless reception device for receiving a signal transmitted from the wireless transmission device, an information extracting device for extracting the position-detection signal from the signal received by the wireless reception device, an identification-information storing device for storing identification information including relative positions and relative angles of opening directions of two or more coils of the capsule medical device, a position/orientation calculating device for calculating a position and an orientation of the capsule medical device and a magnetization direction of the magnet on the basis of the identification information read out from the identification-information storing device and the position-detection signal extracted by the information extracting device, a guidance-magnetic-field generating device for generating a guidance magnetic field, and a position-detection-magnetic-field generating device for generating the position-detection magnetic field.

According to the fourth aspect, the position and orientation of the capsule medical device and the magnetization direction of the magnet are calculated with good precision by the operation of the position/orientation calculating device on the basis of the identification information stored in the identification-information storing device provided in the external apparatus and the position-detection signal transmitted from the capsule medical device. In this way, by registering the identification information of the capsule medical device to be used, the capsule medical device can be guided even more smoothly.

In the above-described aspect, the guidance-magnetic-field generating device may be controlled on the basis of the position and the orientation of the capsule medical device and the magnetization direction of the magnet calculated by the position/orientation calculating device.

In this way, an optimal guidance magnetic field can be generated on the basis of the position and orientation of the capsule medical device and the magnetization direction of the magnet, and the capsule medical device can be guided even more smoothly.

A fifth aspect of the present invention provides a capsule medical device which is introduced to the inside of a subject to acquire bio information of the subject and to receive a position-detection signal transmitted from an external apparatus, the capsule medical device including a bio-information acquiring device (bio-information detecting device) for acquiring bio information of the subject; a signal receiving device for carrying out an reception operation of the position-detection signal in synchronization with the operation of the bio-information acquiring device; and a wireless transmission device for transmitting the bio information acquired by the bio-information acquiring device, information of the position-detection signal received by the signal receiving device, and a sync signal which is synchronized with the operation of the signal receiving device.

With the capsule medical device having such a configuration, since the signal receiving device and the wireless transmission device operate in synchronization, the signal receiving device can be operated in a state in which the condition of the position-detection signal, such as the phase of the position-detection signal generated by the external apparatus (position-detection signal generating device), is determined in advance, and thus, the signal receiving device can be operated only in a desired state. In this way, the operating time can be reduced, and the power consumption of the capsule medical device can be suppressed.

Moreover, it is desirable that the bio-information acquiring device periodically detect the bio information of the subject, and the signal receiving device repeat a reception operation and operation stoppage in synchronization with the operation of the bio-information acquiring device.

With the capsule medical device having such a configuration, since the signal receiving device alternates between a reception operation and operation stoppage (in other words, operates intermittently), power consumption can be reduced.

Moreover, with this capsule medical device, since a sync signal synchronized with the operation period of the signal receiving device is generated at the wireless transmission device, the period in which the signal receiving device is operating can be determined on the basis of this sync signal. In this way, the external apparatus (position-detection signal generating device) for generating the position-detection signal can be operated for only the period in which the signal receiving device is operating and can be stopped for other periods, and thus, power consumption of the external apparatus can be reduced.

Here, the bio-information acquiring device may be an image-acquisition unit for acquiring an image of the inside of the subject and for outputting an image signal, and the sync signal may a signal included, in advance, in the image signal output from the image-acquisition unit.

In such a case, the external apparatus can be synchronized by using a signal originally contained in the image signal (for example, a sync signal). In this way, the capsule medical device according to the present invention can be obtained by only slightly modifying a conventional capsule medical device.

The sync signal may be a vertical sync signal of the image signal or may be a horizontal sync signal of the image signal.

When the capsule medical device has a data compressing device for compressing the image information captured by the image-acquisition unit to generate a compressed image signal, the vertical sync signal of the image signal and the horizontal sync signal of the image signal are also compressed, and these sync signals cannot be directly detected from the compressed image signal. In such a case, data that specifies the position of the compressed data signal (for example, a header data block of the compressed image signal) may be detected and used as a sync signal.

The capsule medical device may have a configuration in that the signal receiving device operates in a period different from an operation period of the bio-information acquiring device.

In such a case, since one of the bio-information acquiring device and the signal receiving device is stopped during the period in which the other operates, a reduction in the voltage supplied to the power supply of the capsule medical device during operation of these devices is suppressed, and thus the effect due to a reduction in the supplied voltage to the devices installed in the capsule medical device can be reduced.

A sixth aspect of the present invention provides a capsule medical device system including the above-described capsule medical device, according to the present invention, that is introduced into a subject, acquires bio information of the subject, and wirelessly transmits the bio information; and an external apparatus provided outside the subject for receiving the bio information generated by the capsule medical device, wherein the external apparatus includes a position-detection signal generating device for wirelessly transmitting a position-detection signal, a wireless reception device for receiving a signal generated by the wireless transmission device of the capsule medical device, a sync-signal extracting device for extracting the sync signal from the signal received by the wireless reception device, and a synchronization device for synchronizing a generation timing of the position-detection signal of the position-detection signal generating device and the operation timing of the signal receiving device of the capsule medical device on the basis of the sync signal extracted at the sync-signal extracting device.

With the capsule medical device system having such a configuration, since the signal receiving device and the wireless transmission device operate in synchronization, the signal receiving device can be operated in a state in which the condition of the position-detection signal, such as the phase of the position-detection signal generated by the external apparatus (position-detection signal generating device), is determined in advance, and thus, the signal receiving device can be operated only in a desired state. In this way, the operating time can be reduced, and the power consumption of the capsule medical device can be suppressed.

Power consumption of the capsule medical device can be reduced by alternately repeating the operation and stoppage of the signal receiving device of the capsule medical device (in other words, operating intermittently).

The operation timing of the position-detection signal generating device is controlled by the control device. The control device synchronizes the generation timing of the position-detection signal and the operation timing of the signal receiving device of the capsule medical device on the basis of the sync signal generated by the wireless transmission device of the capsule wireless transmission device.

In other words, in this capsule medical device system, the position-detection signal generating device provided outside the subject can be operated for only the period in which the signal receiving device is operating and can be stopped for other periods, and thus, power consumption of the external apparatus can be reduced.

Here, the signal receiving device of the capsule medical device may be constructed to receive a plurality of the position-detection signals in a plurality of operations carried out at predetermined intervals, and the position/orientation calculating device may include a frequency selecting unit for extracting a frequency component corresponding to the position-detection signal received by the wireless reception device, and a position/orientation data processing unit for calculating at least one of position and orientation of the capsule medical device on the basis of the frequency component selected by the frequency selecting unit.

In such a case, the signal received by the wireless reception device of the external apparatus (signal containing the signal transmitted by the wireless transmission device of the capsule medical device) is processed by the frequency selecting unit to extract a frequency component corresponding to the position-detection signal.

In other words, the signal transmitted from the wireless transmission device of the capsule medical device (signal containing a plurality of position-detection signals received by the signal reception device) is extracted from the signal received by the wireless reception device of the external apparatus, and unwanted components, such as noise, are removed.

In this way, the amount of data processing at the position/orientation data processing unit can be reduced. When the position/orientation data processing unit has a storage device (including a storage device for temporary recording) for storing the signal received by the wireless reception device, since only the minimum amount of information required for calculating at least one of the position and orientation of the capsule medical device has to be stored in the storage device, the storage capacity of the storage device can be reduced.

Moreover, the position/orientation calculating device may include an FFT processing unit for performing Fourier transformation of the signal received by the wireless reception device, and the frequency selecting unit may receive a processing result from the FFT processing unit and extract a frequency component corresponding to the position-detection signal.

In such a case, the signal received by the wireless reception device of the external apparatus (signal containing the signal transmitted from the wireless transmission device of the capsule medical device) is processed by the FET processing unit, and the frequency selecting unit extracts a frequency component corresponding to the position-detection signal from the processing result.

In other words, the signal transmitted from the wireless transmission device of the capsule medical device (signal containing a plurality of position-detection signals received by the signal reception device) is extracted from the signal received by the wireless reception device of the external apparatus, and unwanted components, such as noise, are removed.

In this way, the amount of data processing at the position/orientation data processing unit can be reduced. When the position/orientation data processing unit has a storage device (including a storage device for temporary recording) for storing the signal received by the wireless reception device, since only the minimum amount of information required for calculating at least one of the position and orientation of the capsule medical device has to be stored in the storage device, the storage capacity of the storage device can be reduced.

Furthermore, the capsule medical device may have a magnet therein; the external apparatus may include a guidance-magnetic-field generating device for generating a guidance magnetic field which acts on the magnet to guide the capsule medical device; and the signal receiving device of the capsule medical device may include a filter device for removing a frequency component contained in the guidance magnetic field.

When a magnetic field acts on the signal receiving device of the capsule medical device, an induction signal is generated by magnetic induction.

Thus, as described above, by providing a filter device for the signal receiving device, among the generated induction signals, the induction signal due to the guidance magnetic field is attenuated. In this way, since the effect of the guidance magnetic field on the position-detection signal received by the signal receiving device is reduced, the position-detection signal can be accurately detected, and thus the position-detection precision of the capsule medical device is improved to perform smooth guiding of the capsule medical device.

The present invention has an advantage in that a capsule medical device can be smoothly guided through the inside of a body cavity by applying a magnetic field from the outside of the body.

Furthermore, with the capsule medical device and the capsule medical device system according to the present invention, power consumption can be reduced while satisfactorily performing position detection of the capsule medical device.

Figure 1:
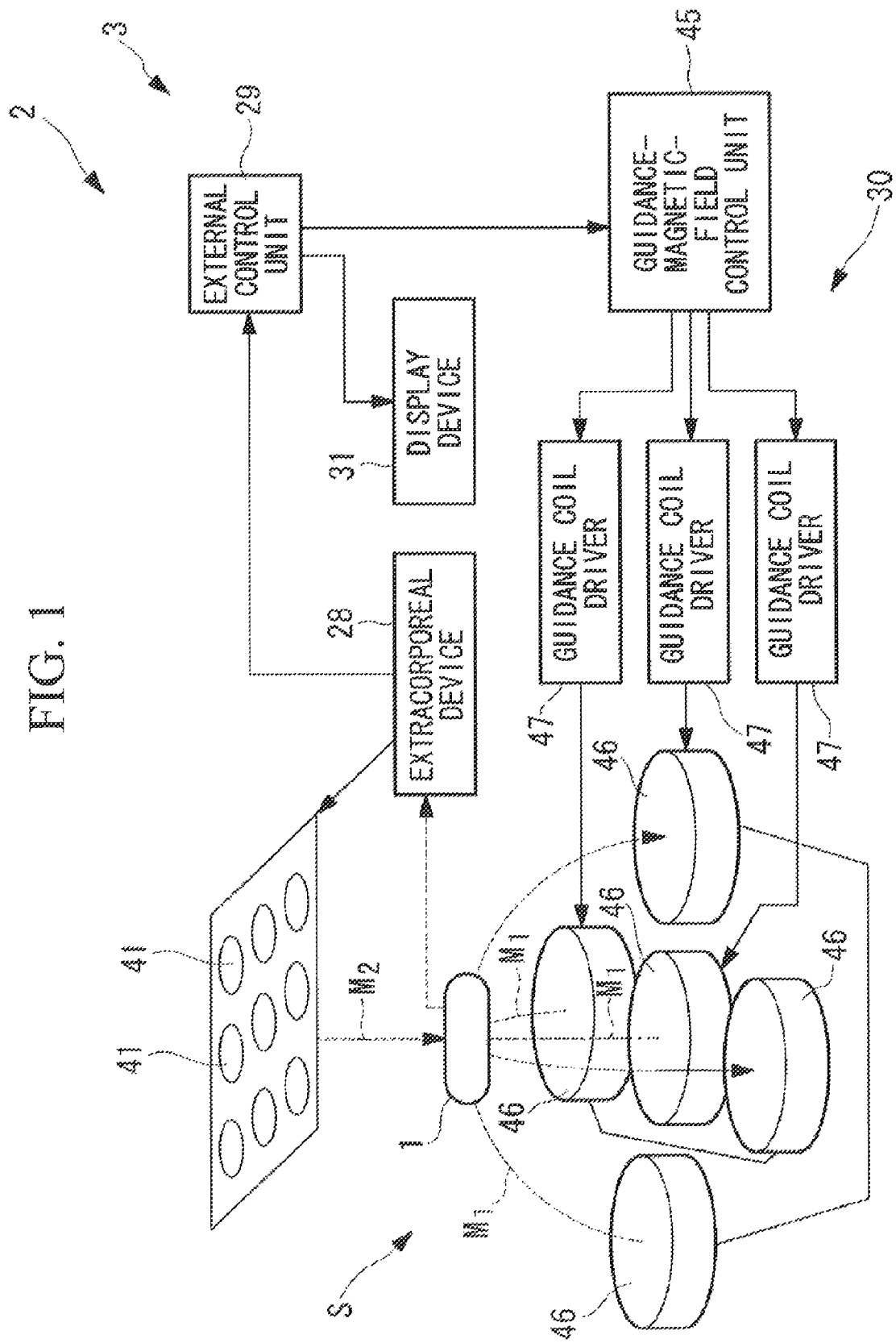
FIG. 1 illustrates the entire configuration of a capsule medical device system according to a first embodiment of the present invention.

EXPLANATION OF REFERENCE SIGNS $M_1$: guidance magnetic field
$M_2$: position-detection magnetic field
1, 1': capsule medical device
2: capsule medical device system
3: external apparatus
5: image-acquisition unit (bio-information detecting device)
7, 7a, 7b: coil
8: filter (filter device)
9: position-detection signal processing unit (position-detection signal processing device)
10: wireless transmitter (wireless transmission device)
12: permanent magnet (magnet)
30: guidance-magnetic-field generating unit (guidance-magnetic-field generating device)
33: wireless receiver (wireless reception device)
34: data separating unit (position-detection-signal extracting device)
38: position-detection-magnetic-field generating unit (position-detection-magnetic-field generating device)
43: position/orientation calculating unit (position/orientation calculating device)
52: switching unit (switching device)
101: capsule medical device
102: capsule medical device system
103: external apparatus
105: image-acquisition unit (bio-information acquiring device)
106: power supply
108: filter
110: wireless transmitter
130: guidance-magnetic-field generating unit
133: wireless receiver
138: position-detection-magnetic-field generating unit (position-detection-signal generating device)
139: trigger detecting unit (sync-signal extracting device)
140: position/orientation-detection signal generating unit (synchronization device)

143: position/orientation calculating unit (position/orientation data processing unit)
143a: FFT processing unit
143b: frequency selecting unit
112: permanent magnet
Re: signal receiving device

BEST MODE FOR CARRYING OUT THE INVENTION

A capsule medical device 1 and a capsule medical device system 2 according to a first embodiment of the present invention will be described below with reference to FIGS. 1 to 8.

Figure 2:
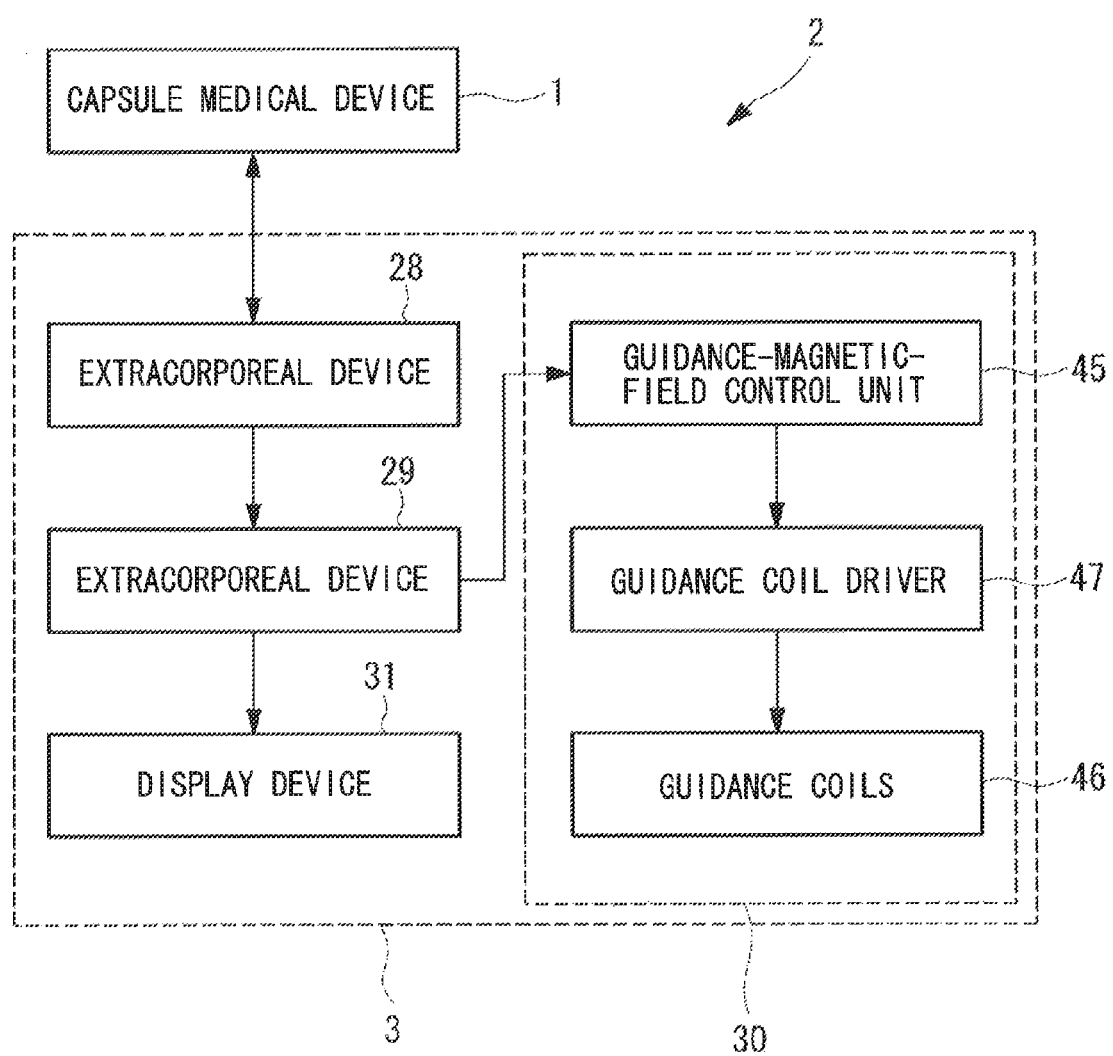
FIG. 2 is a block diagram of the capsule medical device system shown in FIG. 1.

As shown in FIGS. 1 and 2, the capsule medical device system 2 according to this embodiment includes the capsule medical device 1 introduced into a body cavity of a subject (not shown) and an external apparatus 3 disposed outside the subject's body.

Figure 3:
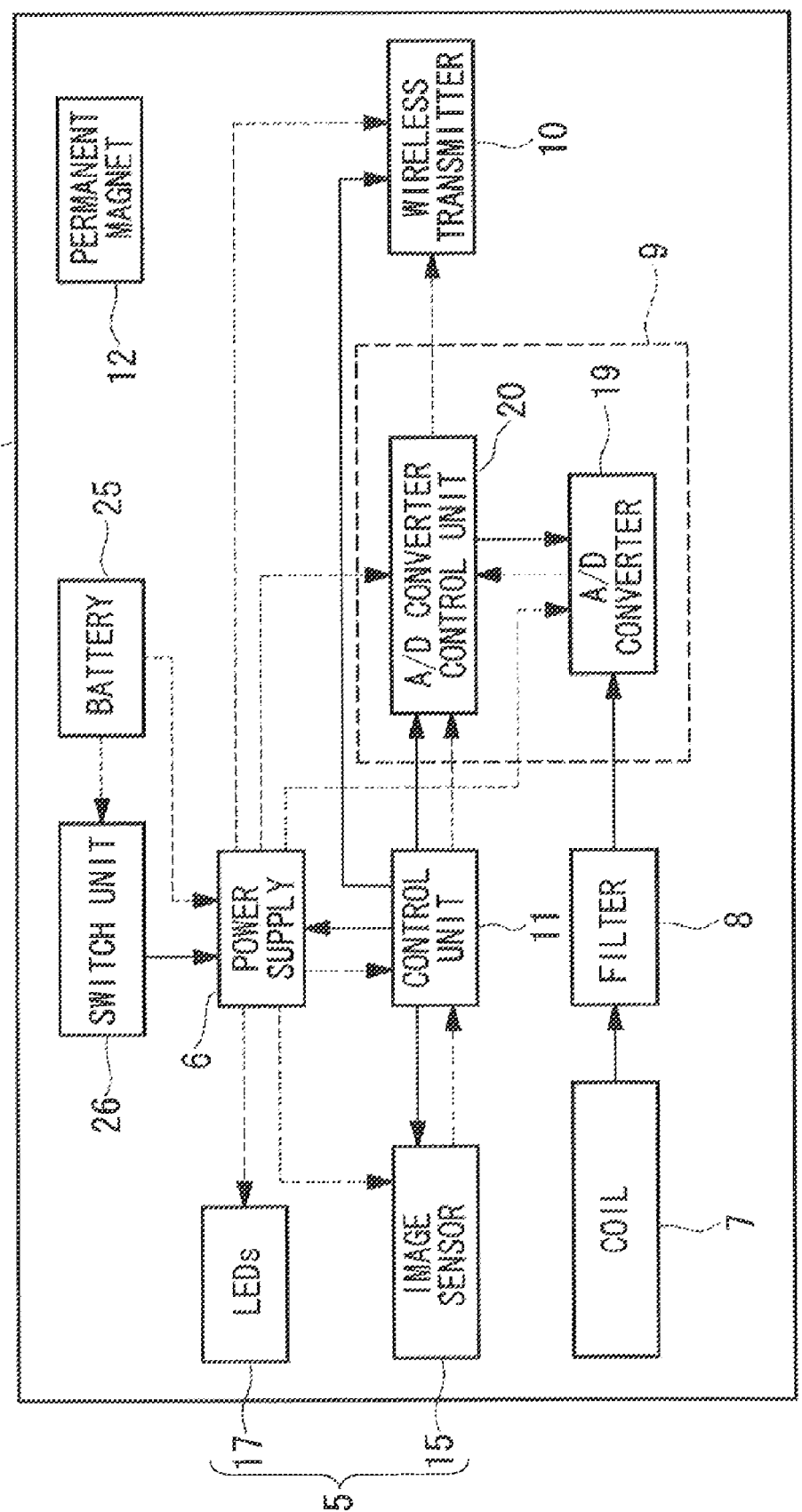
FIG. 3 is a block diagram of a capsule medical device according to this embodiment.
Figure 4:
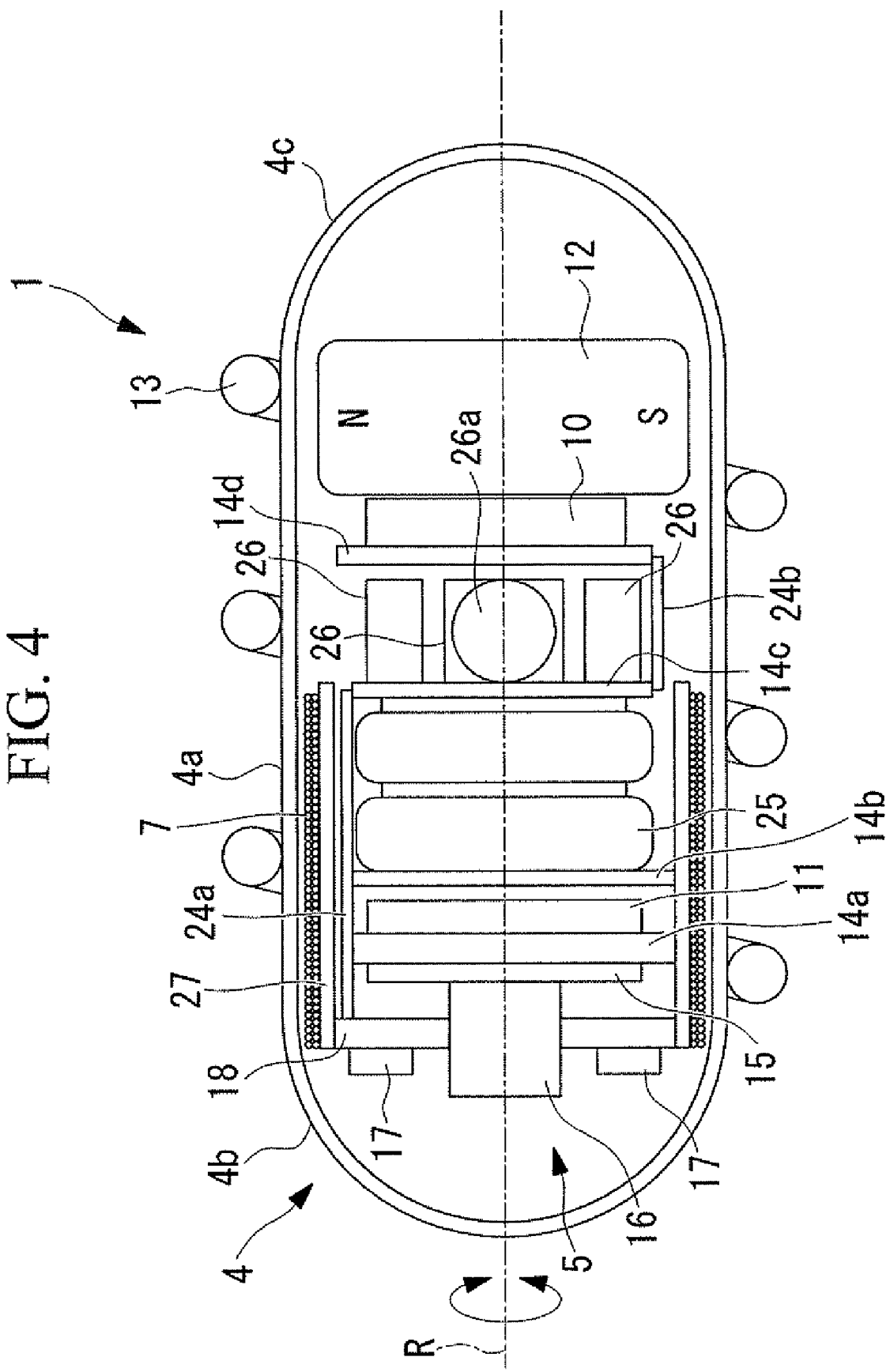
FIG. 4 is a longitudinal cross-sectional view of the capsule medical device shown in FIG. 3.

As shown in FIGS. 3 and 4, the capsule medical device 1 includes a case 4 that accommodates various devices; an image-acquisition unit (bio-information detecting device) 5 that captures an image (bio information) of the inside of the body cavity of the subject; a power supply 6 that supplies operating power to the various device inside the case 4; a magnetic-field sensor coil (hereinafter simply referred to as "coil") 7 that generates an induction signal in response to magnetic fields $M_1$ and $M_2$ applied from the external apparatus 3; a filter 8 that filters the induction signal generated at the coil 7; a position-detection-signal processing unit 9 that process a position-detection signal that has passed through the filter 8; a wireless transmitter 10 that transmits the processed position-detection signal to outside of the body; a control unit 11 that controls the power supply 6, the image-acquisition unit 5, the position-detection-signal processing unit 9, and the wireless transmitter 10; and a permanent magnet (magnet) 12 that generates a driving force in response to the magnetic fields $M_1$ and $M_2$ applied from the external apparatus 3.

The case 4 is formed of a cylindrical capsule body 4a that has a center axis aligned with a longitudinal axis R of the capsule medical device 1 and that is transparent to infrared, a transparent hemispherical forward end section 4b that covers the forward end of the capsule body 4a, and a hemispherical rear end section 4c that covers the rear end of the capsule body 4a. The case 4 forms a sealed capsule container having a liquid-tight structure.

The outer circumferential surface of the capsule body 4a of the case 4 includes a helical section 13 formed by spirally winding a wire, having a circular cross-section, around the longitudinal axis R.

The image-acquisition unit 5 includes an image sensor 15 that is disposed on a surface on the forward end section 4b side of a substrate 14a disposed substantially orthogonal to the longitudinal axis R, a lens group 16 that forms an image of the inner surface of the body cavity of the subject at the image sensor 15, and light emitting diodes (LEDs) 17 that illuminate the inner surface of the body cavity.

The image sensor 15 converts the imaged light to an electrical signal (image signal) via the forward end section 4b and the lens group 16 and outputs the electrical signal to the control unit 11. The image sensor 15 is, for example, a complementary metal oxide semiconductor (CMOS) or a charge coupled device (CCD).

The LEDs 17 are disposed on a support member 18, which is disposed closer to the forward end section 4b than the substrate 14a, with gaps provided in the circumferential direction with respect to the center of the longitudinal axis R.

The filter 8 is, for example, provided on the substrate 14a and is, for example, a first-order high-pass filter having a cutoff frequency of approximately 1 kHz.

The position-detection-signal processing unit 9 includes an A/D converter (represented as "ADC" in the drawings) 19 that converts the position-detection signal that has passed through the filter 8 to a digital signal; and an A/D converter control unit (represented as "ADC control unit" in the drawings) 20 that controls the A/D converter 19 and that sends the position-detection signal output from the A/D converter 19 and the image signal acquired by the image sensor 15 to the wireless transmitter 10 at a predetermined timing.

Figure 5:
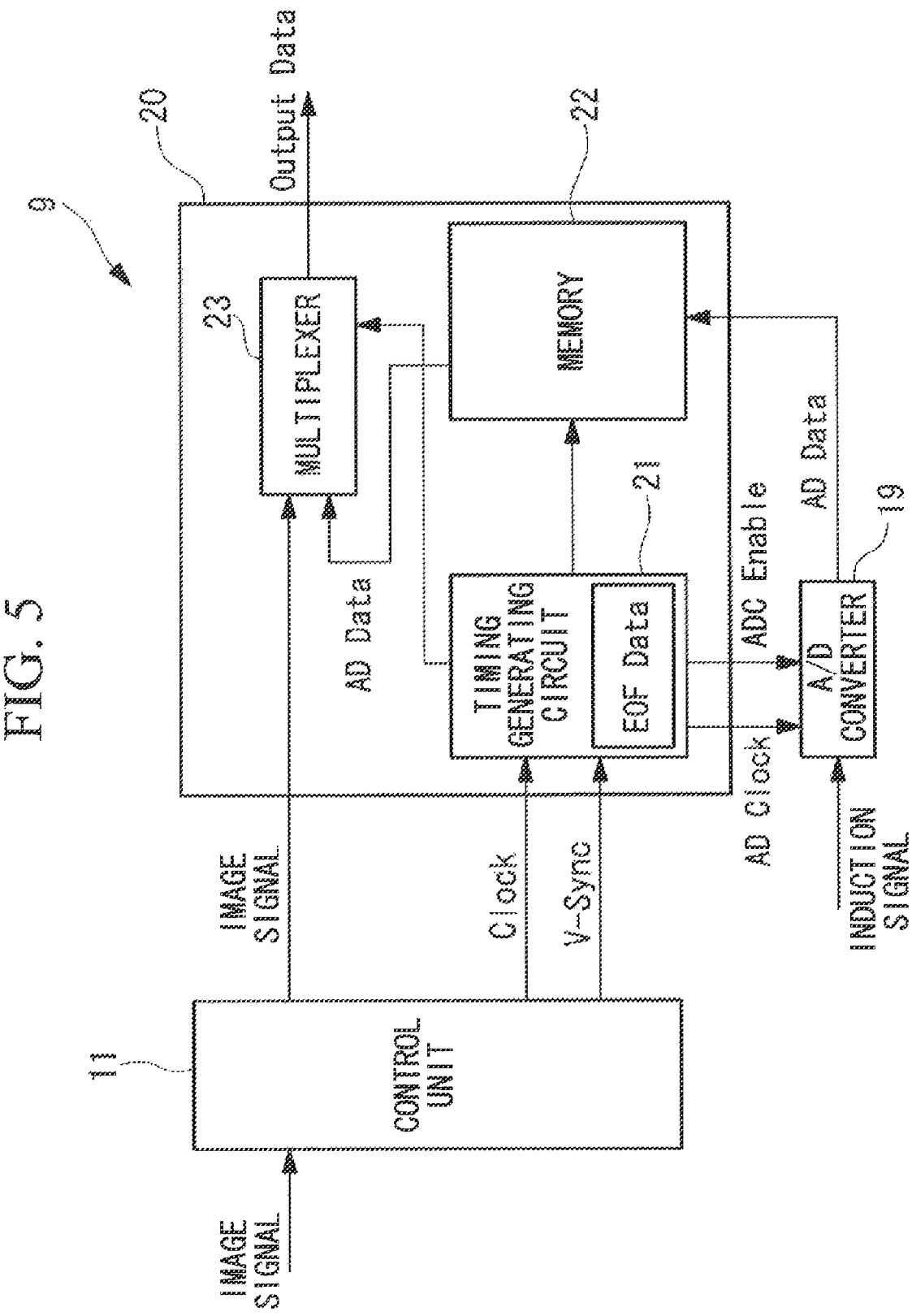
FIG. 5 is a block diagram of a position-detection signal processing unit built into the capsule medical device shown in FIG. 3.

More specifically, as shown in FIG. 5, the A/D converter control unit 20 includes a timing generating circuit 21 that is connected to the control unit 11 and generates a timing signal on the basis of a clock signal Clock received from the control unit 11 and a sync signal (for example, a vertical sync signal V-Sync) obtained from the image signal input to the control unit 11; a memory 22 for storing the digital position-detection signal output from the A/D converter 19; and a multiplexer 23 that is connected to the memory 22, the timing generating circuit 21, and the control unit 11 and that switches the output of the image signal from the control unit 11 and the position-detection signal from the memory 22 based on the timing signal from the timing generating circuit 21. The timing generating circuit 21 outputs a clock signal AD Clock and an A/D conversion enable signal to the A/D converter 19.

The control unit 11 is electrically connected to a battery 25 via substrates 14a to 14d and flexible substrates 24a and 24b, is electrically connected to the image sensor 15 via the substrate 14a, and is electrically connected to the LEDs 17 via the flexible substrate 24a and the support member 18. The control unit 11 outputs the image signal acquired by the image sensor 15 to the A/D converter control unit 20 and turns on or off the image sensor 15 and the LEDs 17.

The control unit 11 controls the wireless transmitter 10 to transmit the signal output from the multiplexer 23 of the A/D converter control unit 20 to the outside.

In other words, the wireless transmitter 10, for example, transmits data containing a sequence of image signals and position-detection signals, having predetermined lengths, to the outside.

The permanent magnet 12 is disposed at the rear end section 4c side of the wireless transmitter 10. The permanent magnet 12 is disposed or magnetized such that the magnetization direction (magnetic pole) is orthogonal (for example, the vertical direction in FIG. 4) to the longitudinal axis R. Switch units 26, which are disposed on the substrate 14c, are provided at the forward end section 4b side of the permanent magnet 12. Each switch unit 26 includes an infrared sensor 26a, is electrically connected to the power supply 6, and is electrically connected to the battery 25 via the substrate 14c and the flexible substrate 24a.

The plurality of switch units 26 are arranged in the circumferential direction around the longitudinal axis R and are disposed such that the infrared sensors 26a face outwards in the diameter direction. In this embodiment, a case in which four switch units 26 are provided is described. However, the number of switch units 26 is not limited to four, and, instead, any number of switch units 26 may be provided.

The battery 25 is disposed between the substrates 14b and 14c on the forward end section 4b side of the switch units 26.

The coil 7 is wound inward in the radial direction of the capsule body 4a of the case 4 to form a cylinder. In the drawings, reference number 27 represents a core member (magnetic core) composed of ferrite formed into a cylinder having a center axis that is substantially aligned with the longitudinal axis R.

In this way, the opening direction of the coil 7 is a direction orthogonal to the magnetization direction of the permanent magnet 12. As a result, the magnetic field generated by the permanent magnet 12 is prevented from passing through the inner section of the coil 7, and thus, the magnetic field generated by the permanent magnet 12 does not affect the induction signal generated at the coil 7.

Figure 6:
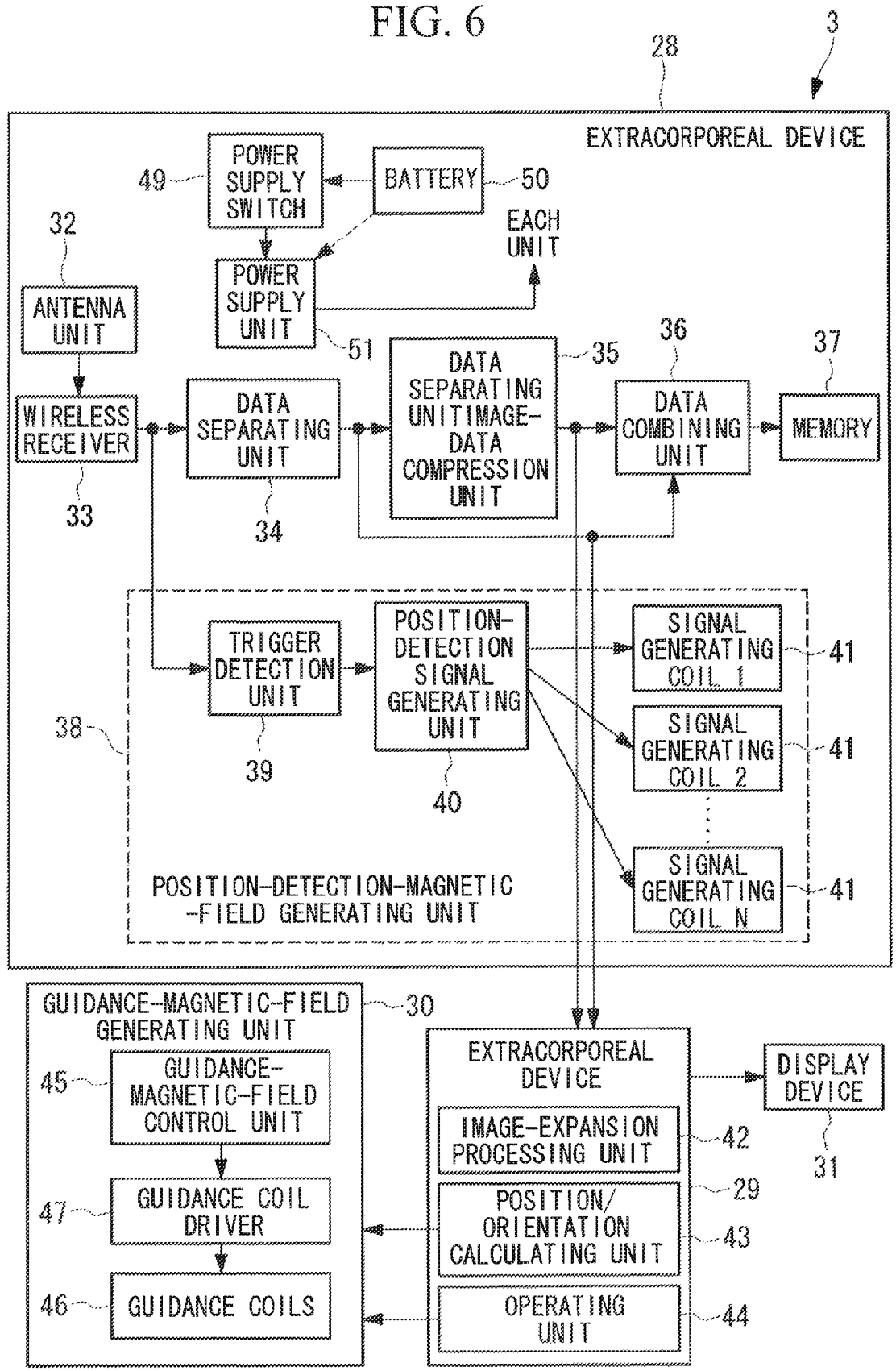
FIG. 6 is a block diagram of an external apparatus of the capsule medical device system shown in FIG. 1.

As shown in FIGS. 2 and 6, the external apparatus 3 includes an extracorporeal device 28 that receives a signal from the capsule medical device 1 and generates a position-detection magnetic field $M_2$; an external control unit 29 that generates an image on the basis of the signal received from the extracorporeal device 28 and calculates at least one of the position and orientation of the capsule medical device 1; a guidance-magnetic-field generating unit 30 that generates the guidance magnetic field $M_1$ on the basis of information of the position and orientation of the capsule medical device 1, which is output from the external control unit 29; and a display device 31 that displays an image on the basis of an image signal output from the external control unit 29.

The extracorporeal device 28 includes a wireless receiver 33 that receives the image signal and the position-detection signal from the capsule medical device 1 via an antenna unit 32; a data separating unit 34 that separates the received signal into an image signal and a position-detection signal; an image-data compression unit 35 that compresses the separated image signal; a data combining unit 36 that combines the compressed image signal and the separated position-detection signal; a memory 37 that stores the combined data; and a position-detection-magnetic-field generating unit 38 that generates the position-detection magnetic field $M_2$ on the basis of the signal received by the wireless receiver 33.

The signal received by the wireless receiver 33 includes the image signal and the position-detection signal. Since the image signal has a predetermined length, the data separating unit 34 can easily separate the image signal and the subsequent position-detection signal.

The position-detection-magnetic-field generating unit 38 includes a trigger detection unit 39 that detects a trigger signal, e.g., the vertical sync signal V-Sync, included in the image information; a position-detection signal generating unit 40 that outputs the position-detection signal at a timing based on the detected trigger signal; and a plurality of signal generating coils 41 that generates the position-detection magnetic field $M_2$ on the basis of the signal output from the position-detection signal generating unit 40.

The external control unit 29 includes an image-expansion processing unit 42 that expands the compressed image signal sent from the extracorporeal device 28 and outputs it to the display device 31; a position/orientation calculating unit 43 that calculates the position and orientation of the capsule medical device 1 on the basis of the position-detection signal from the extracorporeal device 28 and outputs these to the display device 31; and an operating unit 44 that allows the operator to instruct the traveling direction and/or traveling speed of the capsule medical device 1 on the basis of the image of the inside of the body cavity displayed on the display device 31 and the position and orientation of the capsule medical device 1.

The position/orientation calculating unit 43 processes the received position-detection signal, extracts a specific frequency signal having a frequency substantially the same as the frequency of the position-detection magnetic field $M_2$ generated by the position-detection signal generating unit 40, and calculates at least one of the position and the orientation of the capsule medical device 1 on the basis of the extracted specific frequency signal.

The guidance-magnetic-field generating unit 30 includes a guidance-magnetic-field control unit 45 that generates a control signal for the guidance magnetic field $M_1$ on the basis of the operation instruction signal output from the external control unit 29 by the operator and information such as the position and orientation of the capsule medical device 1; a plurality of guidance coils 46 that generates the guidance magnetic field $M_1$ on the basis of the control signal from the guidance-magnetic-field control unit 45; and a guidance coil driver 47 that supplies electric currents to the guidance coils 46.

Here, the operation of the filter 8 described above will be described.

The guidance magnetic field $M_1$ generated at the guidance-magnetic-field generating unit 30 is, for example, an intense magnetic field of 1 mT to 1 T. Moreover, the generation direction and the magnetic field intensity of the guidance magnetic field $M_1$ are changed at a frequency of 100 Hz or less in order to control the position and orientation of the capsule medical device 1.

Alternatively, the position-detection magnetic field $M_2$ has a magnetic field intensity of approximately 0.01 µT to 100 µT and a frequency of several to several hundred kHz at the position of the capsule medical device 1.

When the direction of the capsule medical device 1 is to be changed by the guidance magnetic field $M_1$, a magnetic torque is generated by forming an angle between the magnetization direction of the permanent magnet 12 inside the capsule medical device 1 and the direction of the guidance magnetic field $M_1$. The magnetic torque is maximized when the angle between the magnetization direction of the permanent magnet 12 and the direction of the guidance magnetic field $M_1$ is 90°.

The coil 7 inside the capsule medical device 1 generates an induction (voltage) signal upon receiving the magnetic field. If the induction signal is represented by V, then $$V = 2\pi f B S N \cos\theta$$

Here, f represents the frequency of the magnetic field, B represents the intensity of the magnetic field, S represents the cross-sectional area of the coil, N represents the number of windings of the coil 7, and θ represents the angle between the direction of the magnetic field and the opening direction of the coil 7.

For example, when the induction signal V generated at the coil 7 is determined, where the intensity and frequency of the guidance magnetic field $M_1$ are 100 mT and 10 Hz, respectively, the intensity and frequency of the position-detection magnetic field $M_2$ are 1 µT and 10 kHz, respectively, the angle between the opening direction of the coil 7 and the direction of the magnetic field is 60°, the cross-sectional area of the coil 7 is $10 \times 10^{-6}$ m$^2$, and the number of windings of the coil 7 is 400, the induction signal intensity due to the guidance magnetic field $M_1$ is approximately 100 mV, and the induction signal intensity due to the position-detection magnetic field $M_2$ is approximately 2 mV.

Figure 7:
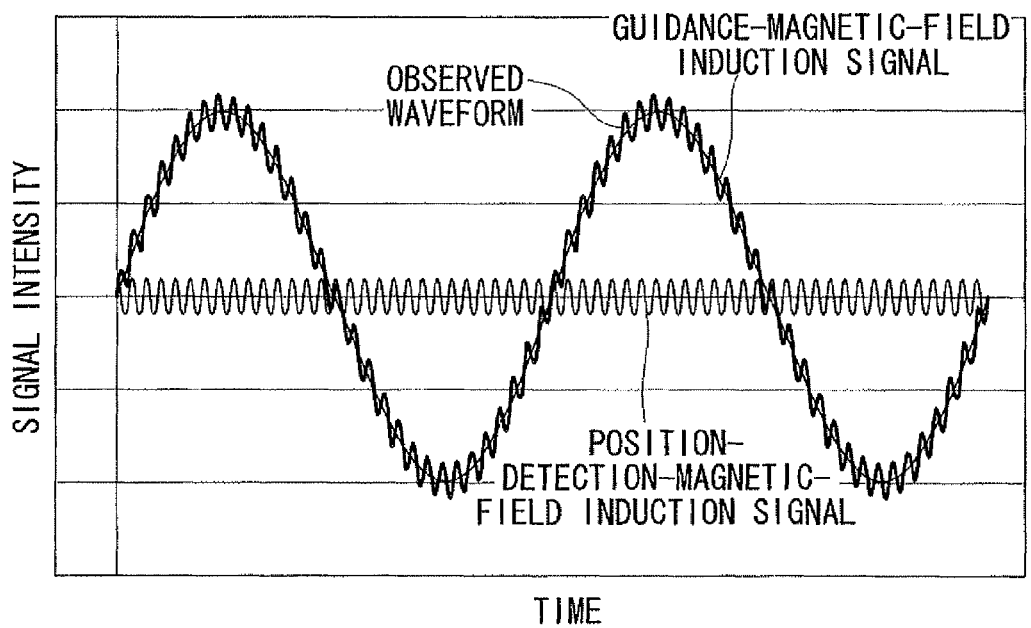
FIG. 7 is a waveform diagram of an example induction signal induced by a magnetic-field sensor coil in the capsule medical device shown in FIG. 3.

The signal detected in this state is illustrated in FIG. 7.

If this signal is directly A/D converted, a large portion of the dynamic range of the A/D converter 19 is used for the induction signal generated by the guidance magnetic field $M_1$, and thus, the induction signal generated by the position-detection magnetic field $M_2$ cannot be detected with good precision.

Figure 8:
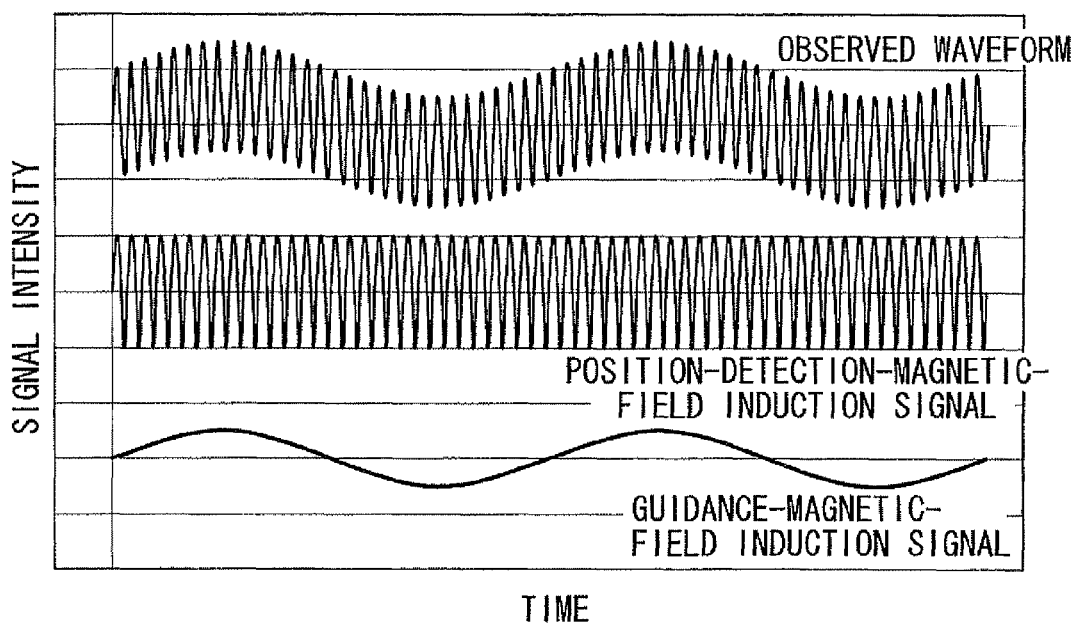
FIG. 8 is a waveform diagram of an example induction signal input to the position-detection signal processing unit in the capsule medical device shown in FIG. 3.

According to this embodiment, by connecting the high-pass filter 8, having a cutoff frequency of approximately 1 kHz, to the coil 7, the induction signal at a frequency of 10 Hz in the guidance magnetic field $M_1$ can be attenuated by −40 dB. In this way, as shown in FIG. 8, the induction signal generated by the guidance magnetic field $M_1$ is attenuated to approximately 1 mV, and the induction signal generated by the position-detection magnetic field $M_2$ is passed at approximately 2 mV.

By connecting the filter 8 to the coil 7 in this way, the effect of the guidance magnetic field $M_1$ is reduced, and the induction signal generated by the position-detection magnetic field $M_2$ can be detected with good precision.

The operation of the capsule medical device 1 and the capsule medical device system 2, according to this embodiment, having the above-described configuration will be described below.

To acquire an image of the inside of the body cavity of the subject using the capsule medical device system 2 according to this embodiment, the subject is disposed in a space S where the guidance magnetic field $M_1$ due to the guidance coils 46, which are disposed as shown in FIG. 1, acts.

Next, the infrared sensor 26a of the capsule medical device 1 is irradiated with infrared rays generated by an infrared generating device, which is not shown in the drawings, to supply power to the capsule medical device 1. Then, the capsule medical device 1 is introduced via the mouth or anus of the subject. In the external apparatus 3, electric power is supplied to each unit by operating a power supply switch 49 of the extracorporeal device 28 with a battery 50 and switching a power supply unit 51 to an ON state.

In the capsule medical device 1 introduced into the body cavity, operation of the image-acquisition unit 5 is started after a predetermined amount of time, and an image of the inner surface of the body cavity illuminated by illumination light from the LEDs 17 is acquired by the image sensor 15. The acquired image signal is sent to the A/D converter control unit 20 via the control unit 11, is further sent to the wireless transmitter 10 at a timing set by the timing generating circuit 21 on the basis of the clock signal Clock and the vertical sync signal V-Sync generated at the control unit 11, and is transmitted outside the body via the wireless transmitter 10.

The transmitted image signal is received by the wireless receiver 33 via the antenna unit 32 provided in the extracorporeal device 28. The received image signal is input to the position-detection-magnetic-field generating unit 38, and a trigger signal, such as the vertical sync signal V-Sync, is detected. Then, the position-detection signal generating unit 40 is started up on the basis of the detected trigger signal, the signal generating coils 41 are energized, and the position-detection magnetic field $M_2$ is generated in the space S where the subject is disposed.

When the generated position-detection magnetic field $M_2$ acts upon the capsule medical device 1, a position-detection signal is induced at the coil 7 by the position-detection magnetic field $M_2$ passing through the inside of the coil 7 in the capsule medical device 1. The position-detection signal is input to the position-detection-signal processing unit 9 via the filter 8, is A/D converted at a timing set by the timing generating circuit 21, and is stored in the memory 22. Then, the position-detection signal is sent to the wireless transmitter 10 via the multiplexer (represented as MUX in the drawings) 23, which is switched at a timing set by the timing generating circuit 21, and is transmitted outside the body via the wireless transmitter 10.

The transmitted position-detection signal is received by the wireless receiver 33 via the antenna unit 32 provided in the extracorporeal device 28. The received position-detection signal is separated from the image signal by the data separating unit 34. The separated position-detection signal is directly sent to the external control unit 29, and the image signal is sent to the external control unit 29 after being compressed at the image-data compression unit 35. The position-detection signal and the compressed image signal are combined in a mutually associated form at the combining unit 36 and are stored in the memory 37.

The image signal sent to the external control unit 29 is expanded at the image-expansion processing unit 42 and is sent to the display device 31 for display. The position-detection signal sent to the external control unit 29 is sent to the position/orientation calculating unit 43 and is used for calculating at least one of the position and the orientation of the capsule medical device 1. The calculated position and orientation of the capsule medical device 1 are sent to the display device 31 for display and are also sent to the guidance-magnetic-field generating unit 30 for calculating the guidance magnetic field $M_1$ to be generated.

After confirming the image of the inner surface of the body cavity and the information of the position and the orientation of the capsule medical device 1 displayed on the display device 31, the operator operates the operating unit 44 of the external control unit 29 in order to input the traveling direction and the traveling speed of the capsule medical device 1 to the guidance-magnetic-field generating unit 30. The guidance-magnetic-field generating unit 30 operates the guidance coil driver 47 such that the intensity and direction of the guidance magnetic field $M_1$ to be generated are achieved on the basis of the instruction signal for the traveling direction and traveling speed input from the operating unit 44 and the information of the position and orientation of the capsule medical device 1 input from the position/orientation calculating unit 43. In this way, the guidance coils 46 are energized, and a desired guidance magnetic field $M_1$ is generated in the space S where the subject is disposed.

When the guidance magnetic field $M_1$ acts upon the capsule medical device 1, the permanent magnet 12 disposed inside the capsule medical device 1 generates a driving force for rotating the capsule medical device 1 to match the magnetization direction to the direction of the guidance magnetic field $M_1$. When the guidance magnetic field $M_1$ is generated in a direction at an angle to the longitudinal axis R of the capsule medical device 1 with respect to the magnetization direction of the permanent magnet 12, a driving force for changing the orientation of the capsule medical device 1 is generated. On the other hand, when the driving force is generated at an angle to the circumferential direction of the capsule medical device 1 with respect to the magnetization direction of the permanent magnet 12, a driving force for rotating the capsule medical device 1 around the longitudinal axis R is generated.

Since the helical section 13 is provided on the outer circumferential surface of the case of the capsule medical device 1, a propulsion force is generated in the direction of the longitudinal axis R by the helical section 13 when the capsule medical device 1 rotates around the longitudinal axis R due to the driving force. In this way, the capsule medical device 1 is propelled in the direction of the longitudinal axis R.

In this case, the coil 7 disposed in the capsule medical device 1 receives both the guidance magnetic field $M_1$ and the position-detection magnetic field $M_2$ and generates induction signals corresponding to the intensity etc. of the guidance magnetic field $M_1$ and position-detection magnetic field $M_2$. However, in the capsule medical device 1 and the capsule medical device system 2 according to this embodiment, since the filter 8 is connected to the coil 7, the induction signal due to the guidance magnetic field $M_1$ is A/D converted in an attenuated state and is transmitted to the external apparatus 3. Therefore, at the external apparatus 3, as described above, the effect of the guidance magnetic field $M_1$ can be reduced, and the position-detection signal-generated by the position-detection magnetic field $M_2$ can be detected with good precision.

Accordingly, since the position and orientation of the capsule medical device 1 are accurately calculated by using the position-detection signal for position detection detected with good precision in this way, the guidance-magnetic-field control unit 45 can drive the guidance coil driver 47 so as to generate the guidance magnetic field $M_1$ accurately corresponding to the instructions from the operator. As a result, there is an advantage in that the capsule medical device 1 can be guided with good precision, and an image of a desired site inside the body cavity can be acquired.

With the capsule medical device system 2 according to this embodiment, since the capsule medical device 1 and the external apparatus 3 are operated in synchronization at a timing generated on the basis of the vertical sync signal V-Sync extracted from the image signal, the capsule medical device 1 can perform A/D conversion on the position-detection signal from the coil 7 only when the position-detection magnetic field $M_2$ is generated by the extracorporeal device 28. Therefore, the processing of the position-detection signal by the position-detection-signal processing unit 9 can be stopped while the position-detection magnetic field $M_2$ is not generated, and thus, power can be conserved.

In this embodiment, the capsule medical device 1 and the external apparatus 3 are synchronized at a timing based on the vertical sync signal V-Sync extracted from the image signal. However, the present invention is not limited thereto, and synchronization may be carried out at a timing based on other trigger signals, such as a horizontal sync signal extracted from the image signal.

A high-pass filter having a cutoff frequency of 1 kHz is used as the filter. Instead, however, a band-pass filter may be used.

In this embodiment, the helical section 13 is provided on the outer circumferential surface of the capsule medical device 1, and the capsule medical device 1 is propelled by rotation. However, the position of the capsule medical device 1 may be controlled by using a magnetic gradient caused by a change in the magnetic field distribution of the guidance magnetic field $M_1$ to generate a force (propulsion force) at the permanent magnet 12.

Next, a capsule medical device 1' and a capsule medical device system according to a second embodiment of the present invention will be described with reference to FIGS. 9 and 10.

In the description of this embodiment, components that have the same configuration as those in the capsule medical device 1 and the capsule medical device system 2 according to the first embodiment are represented by the same reference numerals, and descriptions thereof are omitted.

The capsule medical device 1' according to this embodiment includes two magnetic-field coils (hereinafter, simply referred to as "coils") 7a and 7b in the case 4. As shown in FIG. 10, the two coils 7a and 7b are wound such that their openings are inclined with respect to the longitudinal axis R of the capsule medical device 1'. The opening directions of the two coils 7a and 7b are set in different directions from each other.

Figure 10:
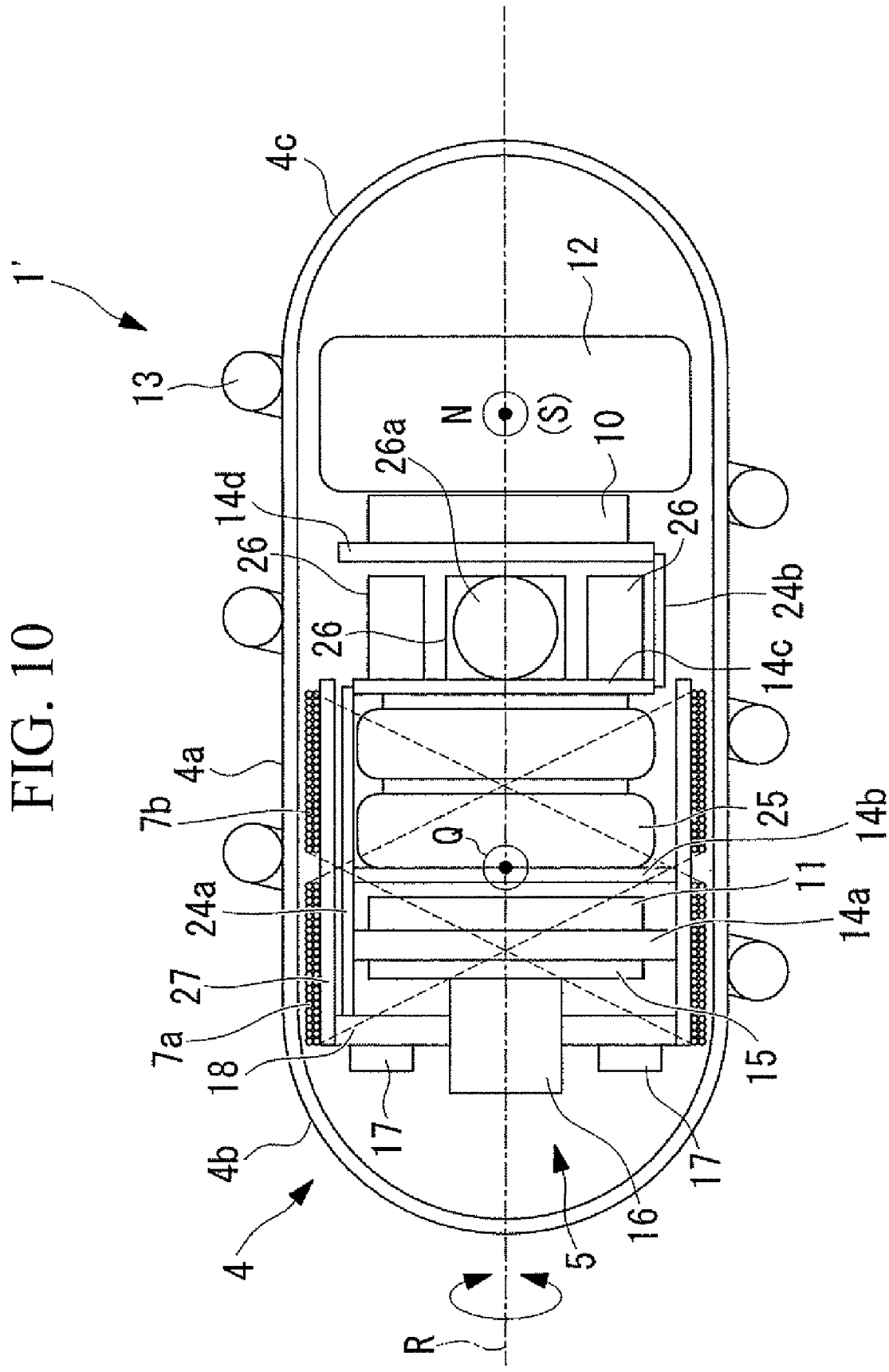
FIG. 10 is a longitudinal sectional view of the capsule medical device shown in FIG. 9.

In the example shown in FIG. 10, the two coils 7a and 7b are disposed in an intersecting manner at the same position in the direction of the longitudinal axis R. In this way, the two coils 7a and 7b have a common radial axis Q in the direction orthogonal to the plane of the drawing of FIG. 10. The magnetization direction of the permanent magnet 12 is disposed parallel to the radial axis Q, i.e., the direction orthogonal to the plane of the drawing of FIG. 10. In this way, the magnetic field generated by the permanent magnet 12 can be prevented, as much as possible, from passing through the two coils 7a and 7b.

Figure 9:
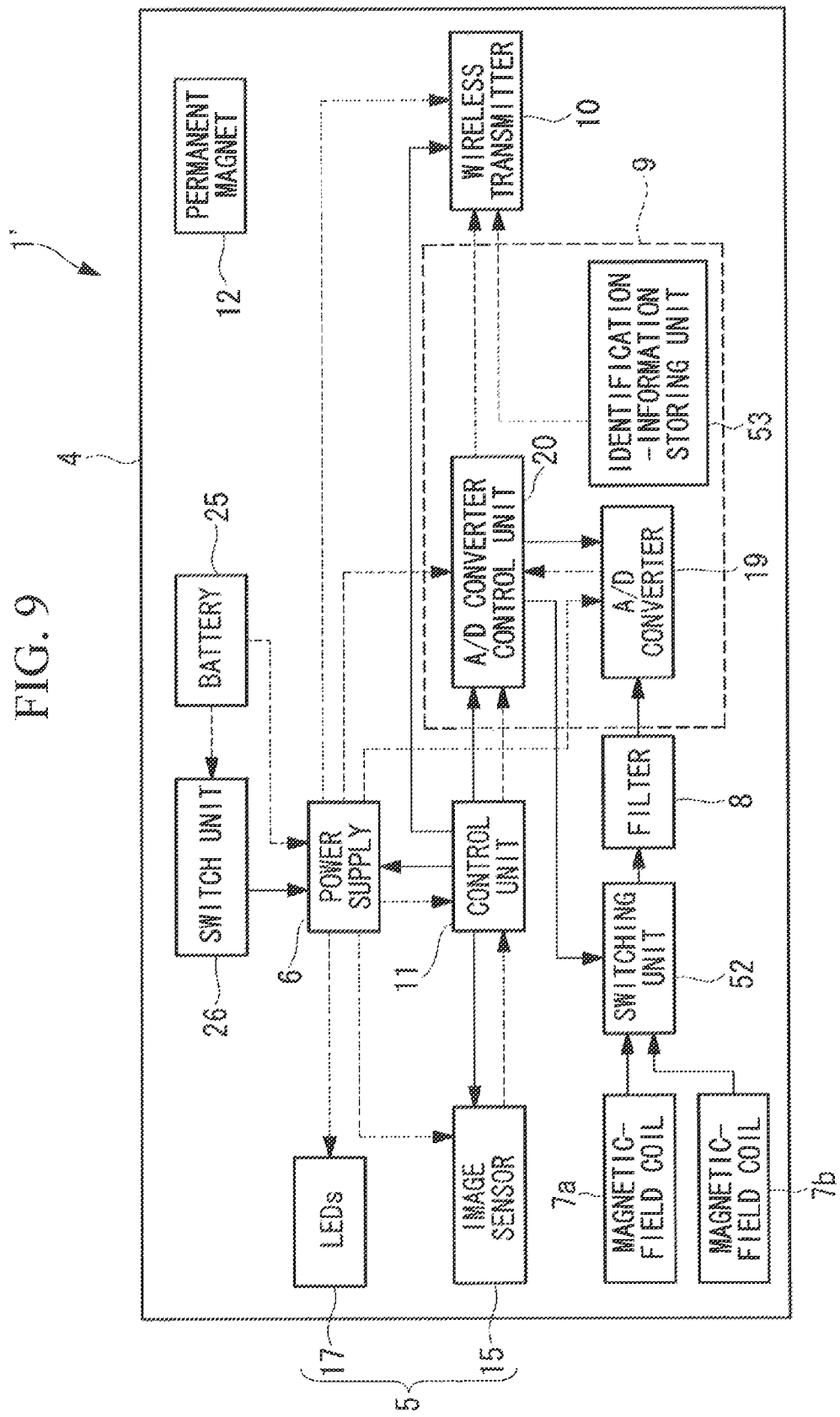
FIG. 9 is a block diagram of a capsule medical device according to a second embodiment of the present invention.

As shown in FIG. 9, the two coils 7a and 7b are connected to the filter 8 via a switching unit 52. The switching unit 52 is connected to the A/D converter control unit 20 and is operated in synchronization with the A/D converter 19 by a timing signal generated at the timing generating circuit 21 of the A/D converter control unit 20.

As shown in FIG. 9, the position-detection-signal processing unit 9 includes an identification-information storing unit 53. The identification-information storing unit 53 holds information such as the positions of the two coils 7a and 7b, the relative angle of the opening direction, the magnetization direction of the permanent magnet 12, and the relative position of the two coils 7a and 7b and the permanent magnet 12. When the capsule medical device 1 is operated, information stored in the identification-information storing unit 53 is sent, at least one time, to the extracorporeal device 28 via the wireless transmitter 10.

The operation of the capsule medical device 1' and the capsule medical device system, according to this embodiment, having such configurations will be described below.

In the capsule medical device system according to this embodiment, when the position-detection magnetic field $M_2$ due to one of the signal generating coils 41 for detecting the position acts upon the capsule medical device 1' by operating the position-detection-magnetic-field generating unit 38 of the extracorporeal device 28, the two coils 7a and 7b in the capsule medical device 1' generate two position-detection signals. Since the two coils 7a and 7b open in different directions, the two position-detection signals differ, except when the direction of the position-detection magnetic field $M_2$ and the direction of the longitudinal axis R are aligned.

The position and orientation of the capsule medical device 1' are determined on the basis of a total of six values: three coordinate values for determining the three-dimensional position and three rotational angle values corresponding to the rotation around the coordinate axes. In the capsule medical device system according to this embodiment, since two position-detection signals are acquired from the magnetic field from one of the signal generating coils 41 for detecting the position, six or more different position-detection signals can be acquired from the capsule medical device 1' in the same position and same orientation by disposing three or more signal generating coils 41 at different positions.

In particular, in the capsule medical device 1' according to this embodiment, since the two coils 7a and 7b are disposed such that the opening directions are inclined with respect to the longitudinal axis R of the capsule medical device 1', even when the same magnetic field acts, different position-detection signals are generated at the two coils 7a and 7b so long as the rotational angles around the longitudinal axis R differ. In this way, the rotational angle around the longitudinal axis R of the capsule medical device 1' can be easily detected.

In this way, in the capsule medical device 1' and the capsule medical device system according to this embodiment, all six degrees of freedom of the capsule medical device 1' can be determined. Therefore, there is an advantage in that even when the direction of the guidance magnetic field and the magnetization direction of the permanent magnet 12 do not match due to friction etc. between the capsule medical device 1' and the surrounding tissue, guidance magnetic field can be detected, and the capsule medical device 1' can be guided with high precision.

In the capsule medical device 1' according to this embodiment, the position-detection signals generated at the two coils 7a and 7b are switched by the operation of the switching unit 52 and are filtered at the filter 8. Therefore, since the induction signal due to the guidance magnetic field $M_1$ is sent to the position-detection-signal processing unit 9 in an attenuated state, the position and orientation of the capsule medical device 1' can be calculated at the external apparatus 3 with high precision.

Since the connection between the two coils 7a and 7b and the filter 8 is switched by the switching unit 52, only one filter 8 is needed, and the size of the capsule medical device 1' can be reduced. Since the switching of the connection between the two coils 7a and 7b and the filter 8 by the switching unit 52 is carried out based on the timing signal generated at the timing generating circuit 21, synchronization with the operation of the position-detection-magnetic-field generating unit 38 of the extracorporeal device 28 is possible, and power consumption thus can be reduced.

In the capsule medical device 1' according to this embodiment, the two coils 7a and 7b are provided. Instead, however, three or more coils may be provided.

Figure 11:
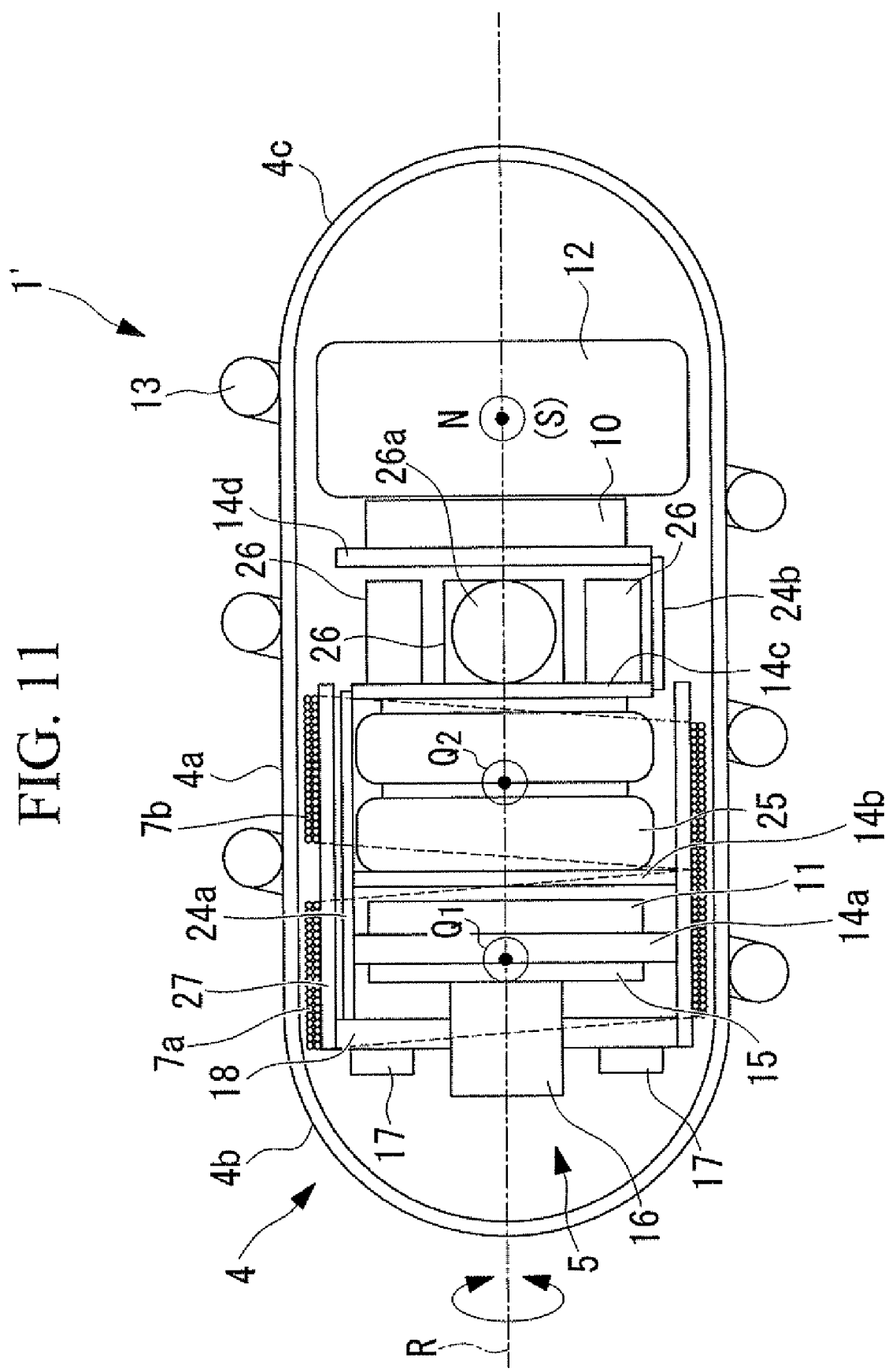
FIG. 11 is a longitudinal sectional view of a modification of the capsule medical device shown in FIG. 10.

In this embodiment, the two coils 7a and 7b are disposed in the same position in the direction of the longitudinal axis R and have a common radial axis Q. Instead, however, as shown in FIG. 11, the two coils 7a and 7b may be disposed in different positions in the direction of the longitudinal axis R. In such a case, the two coils 7a and 7b have parallel radial directions $Q_1$ and $Q_2$, respectively, and the distance between the radial directions $Q_1$ and $Q_2$ is also stored in the identification-information storing unit 53.

In this embodiment, the position-detection-signal processing unit of the capsule medical device 1' has the identification-information storing unit 53 that reads out at least one time after start up. In this way, even when a capsule medical device 1' in which the performance and/or arrangement of the two coils 7a and 7b differs is employed, its position and orientation can be detected with good precision.

Figure 12:
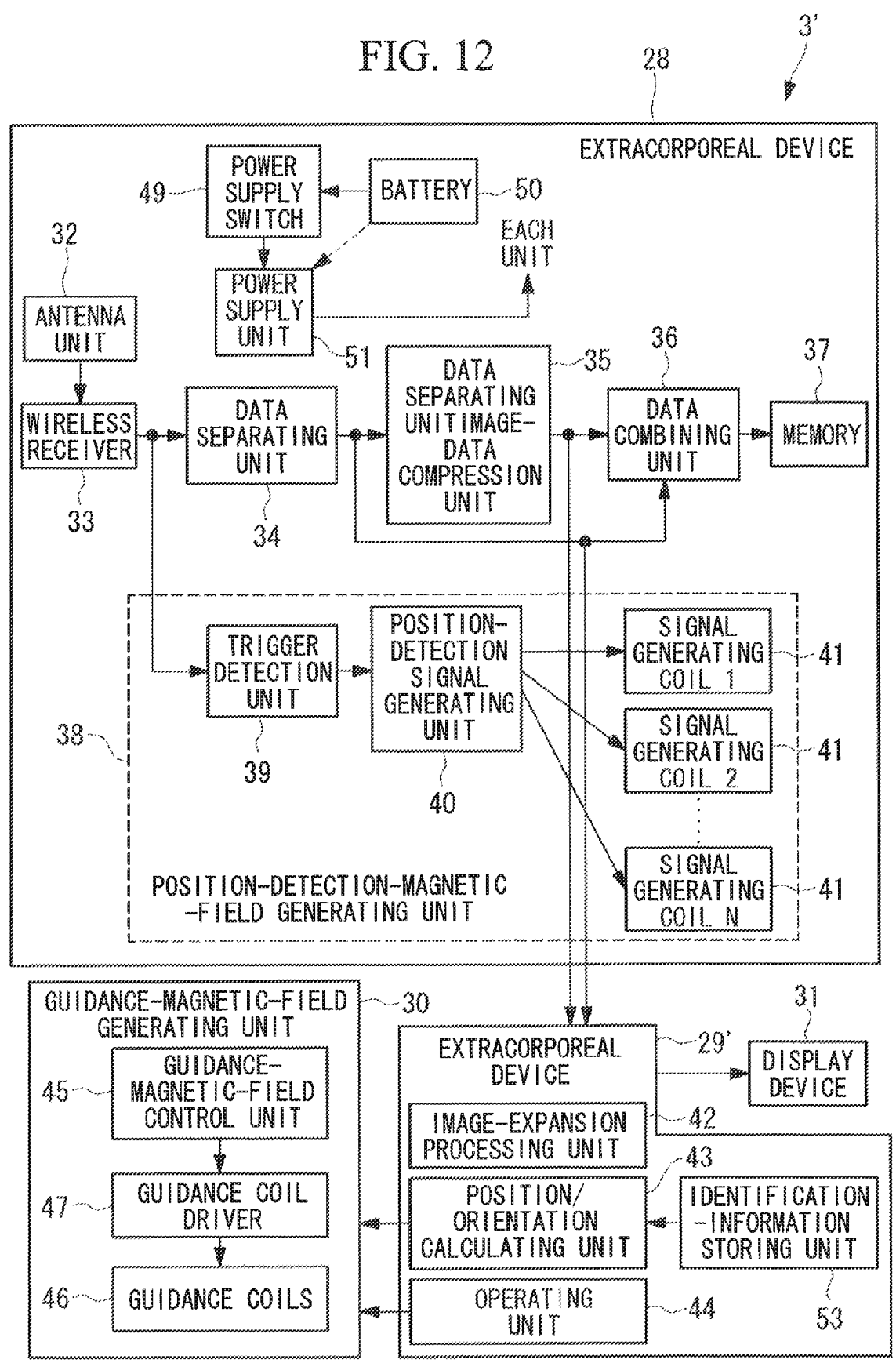
FIG. 12 is a block diagram of a modification of an external apparatus of the capsule medical device system shown in FIG. 6.

Instead, as shown in FIG. 12, the identification-information storing unit 53 may be provided in an external control unit 29' of the external apparatus 3. In such a case, a capsule medical device 1' of a predetermined model must be used. However, identification information does not have to be read out after start up, and the memory capacity of the capsule medical device 1' can be reduced.

A capsule medical device 101 and a capsule medical device system 102 according to the third embodiment of the present invention will be described below with reference to FIGS. 7, 8, and from FIG. 13 to FIG. 18.

Figure 13:
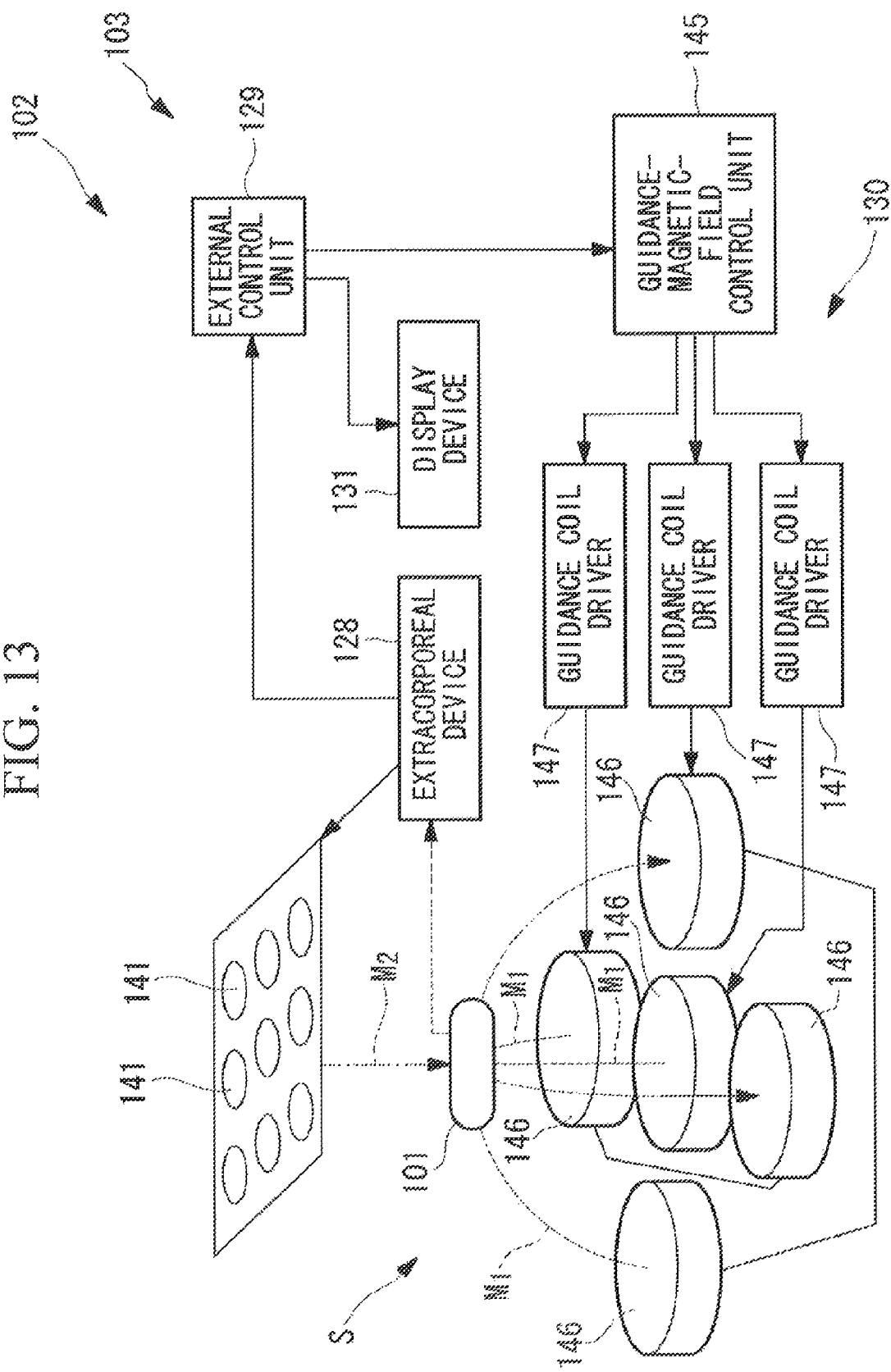
FIG. 13 illustrates the entire configuration of a capsule medical device system according to a third embodiment of the present invention.
Figure 14:
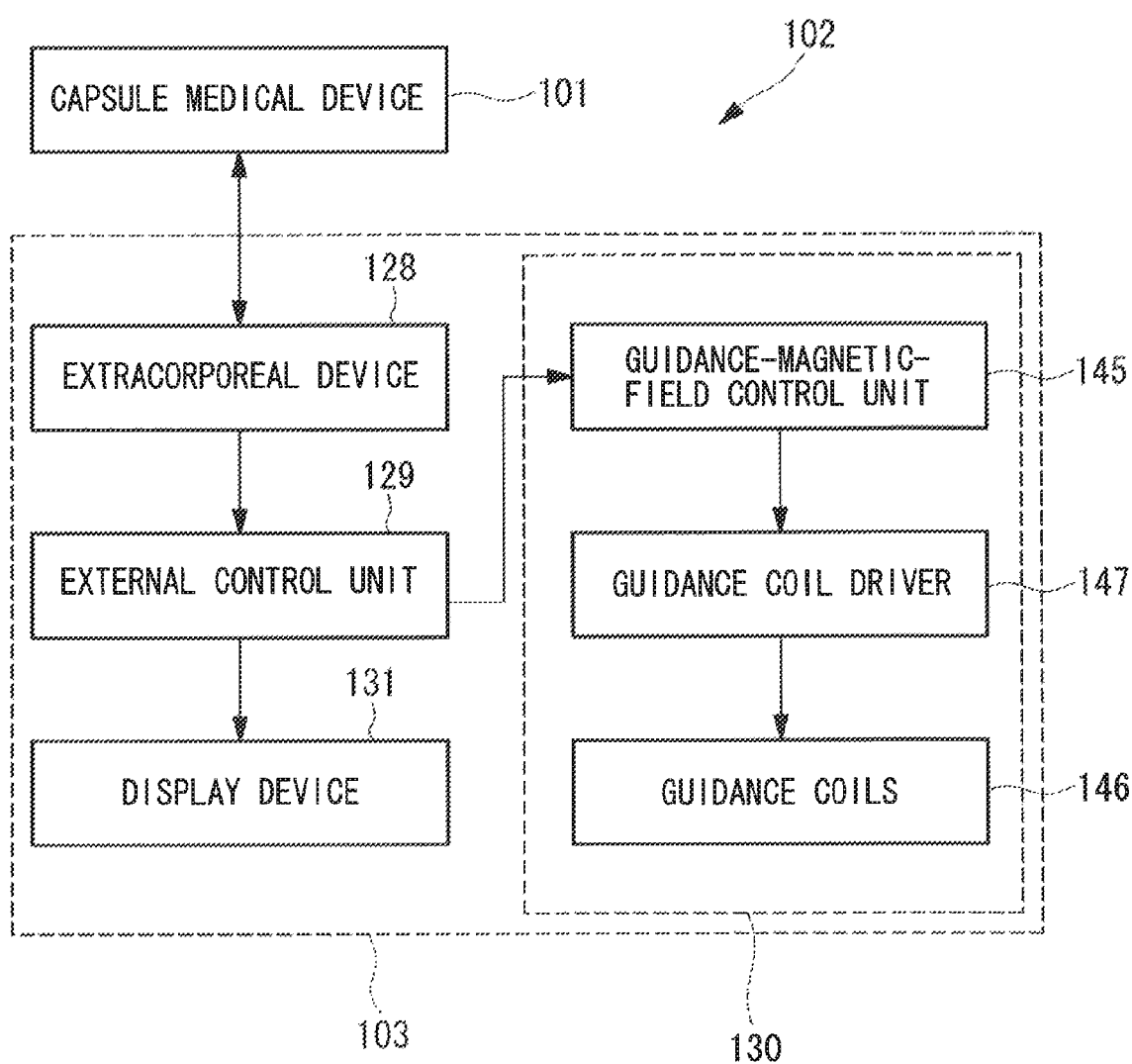
FIG. 14 is a block diagram of the capsule medical device system shown in FIG. 13.

As shown in FIGS. 13 and 14, the capsule medical device system 102 according to this embodiment, includes the capsule medical device 101 introduced into a body cavity of a subject (not shown) and an external apparatus 103 disposed outside the subject's body.

Figure 15:
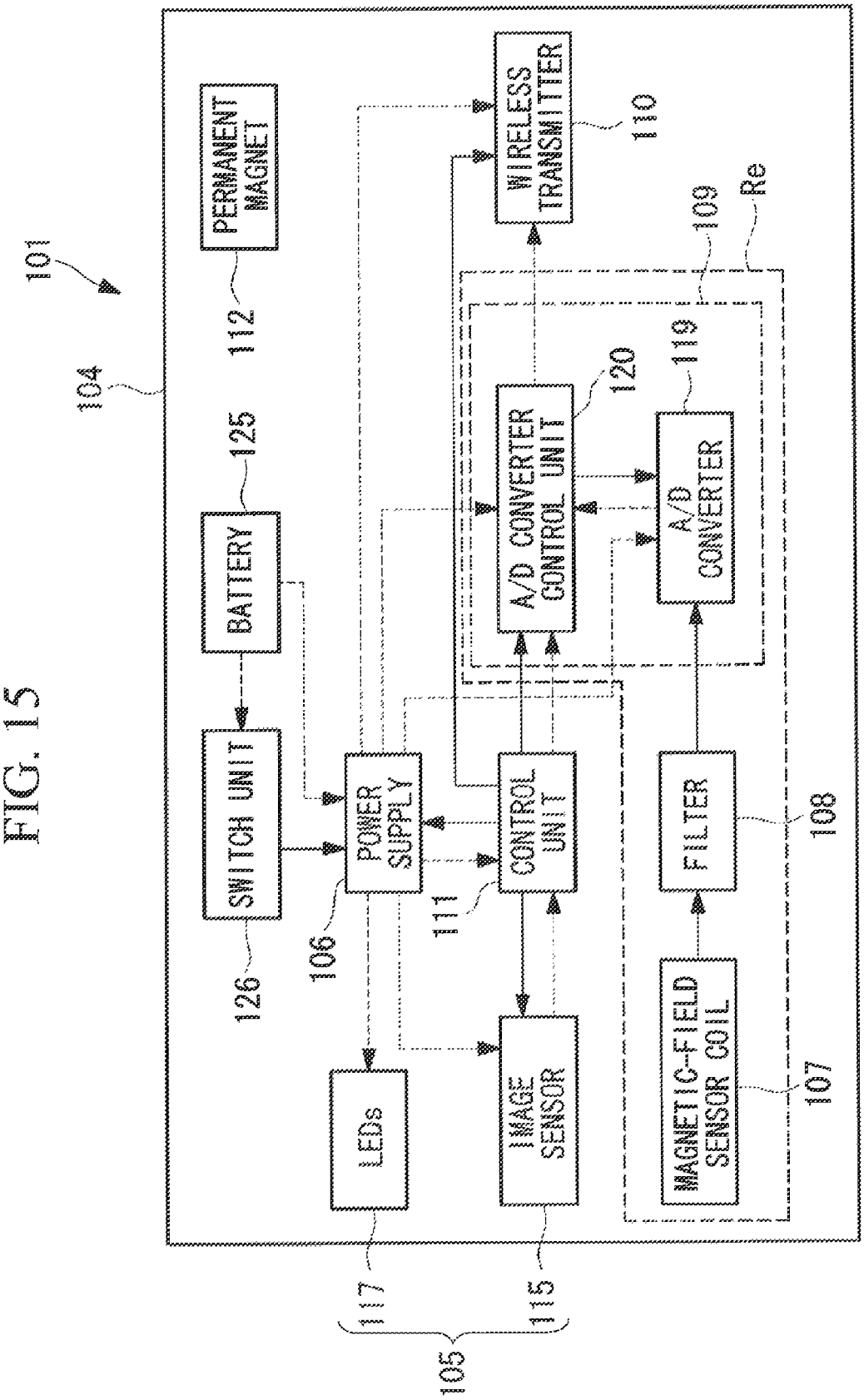
FIG. 15 is a block diagram of a capsule medical device according to the third embodiment of the present invention.
Figure 16:
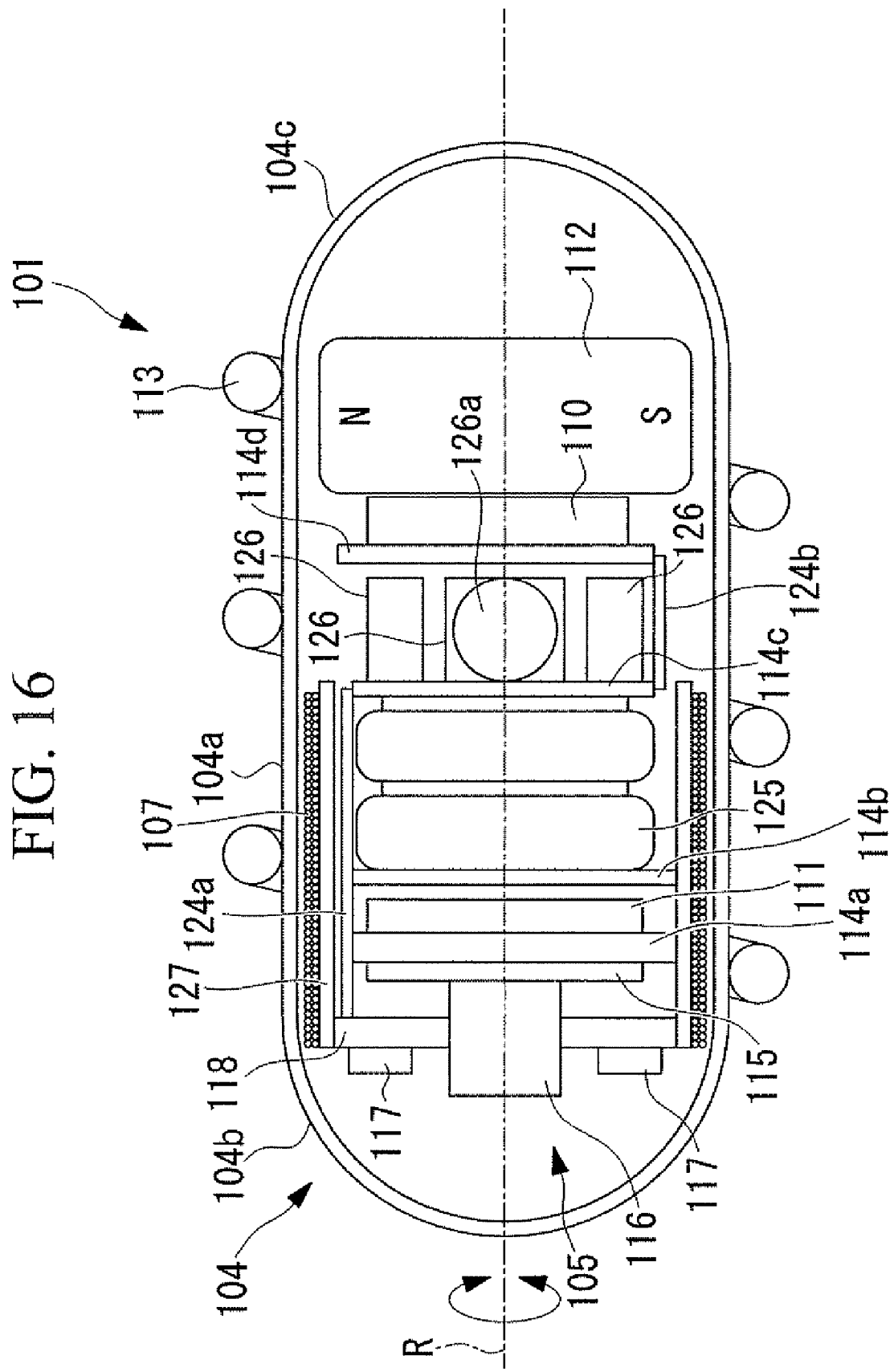
FIG. 16 is a longitudinal sectional view of the capsule medical device shown in FIG. 15.

As shown in FIGS. 15 and 16, the capsule medical device 101 includes a case 104 that accommodates various devices; an image-acquisition unit (bio information acquiring device) 105 that captures an image (bio information) of the inside of the body cavity of the subject; a power supply 106 that supplies operating power to the various device inside the case 104; a magnetic-field sensor coil (hereinafter simply referred to as "coil") 107 that generates an induction signal in response to magnetic fields $M_1$ and $M_2$ applied from the external apparatus 103; a filter 108 that filters the induction signal generated at the coil 107; an induction-signal processing unit 109 that processes an induction signal that has passed through the filter 108; a wireless transmitter 110 that transmits the processed induced signal to outside of the body; a control unit 111 that controls the operations of the power supply 106, the image-acquisition unit 105, the induction-signal processing unit 109, and the wireless transmitter 110; and a permanent magnet (magnet) 112 that generates a driving force in response to the magnetic fields $M_1$ and $M_2$ applied from the external apparatus 103.

As described below, the magnetic field $M_2$ generated at the external apparatus 103 includes a position-detection signal of the capsule medical device 101, and the coil 107, the filter 108, and the induction-signal processing unit 109 constitute a signal receiving device Re that receives a position-detection signal.

The case 104 is formed of a cylindrical capsule body 104a that has a center axis aligned with a longitudinal axis R of the capsule medical device 101 and that is transparent to infrared, a transparent hemispherical forward end section 104b that covers the forward end of the capsule body 104a, and a hemispherical rear end section 104c that covers the rear end of the capsule body 104a. The case 104 forms a sealed capsule container having a liquid-tight structure.

The outer circumferential surface of the capsule body 104a of the case 104 includes a helical section 113 formed by spirally winding a wire, having a circular cross-section, around the longitudinal axis R.

The image-acquisition unit 105 includes an image sensor 115 that is disposed on a surface on the forward end section 104b side of a substrate 114a disposed substantially orthogonal to the longitudinal axis R, a lens group 116 that forms an image of the inner surface of the body cavity of the subject at the image sensor 115, and light emitting diodes (LEDs) 117 that illuminate the inner surface of the body cavity.

The image sensor 115 converts the imaged light to an electrical signal (image signal) via the forward end section 104b and the lens group 116 and outputs the electrical signal to the control unit 111. The image sensor 115 is, for example, a complementary metal oxide semiconductor (CMOS) or a CCD.

The LEDs 117 are disposed on a support member 118, which is disposed closer to the forward end section 104b than the substrate 114a, with gaps provided in the circumferential direction with respect to the center of the longitudinal axis R.

The filter 108 is, for example, provided on the substrate 114a and is, for example, a first-order high-pass filter having a cutoff frequency of approximately 1 kHz.

The induction-signal processing unit 109 includes an A/D converter (represented as "ADC" in the drawings) 119 that converts the induction signal that has passed through the filter 108 to a digital signal; and an A/D converter control unit (represented as "TADC control unit" in the drawings) 120 that controls the A/D converter 119 and that sends the induction-signal output from the A/D converter 119 and the image signal acquired by the image sensor 115 to the wireless transmitter 110 at a predetermined timing.

Figure 17:
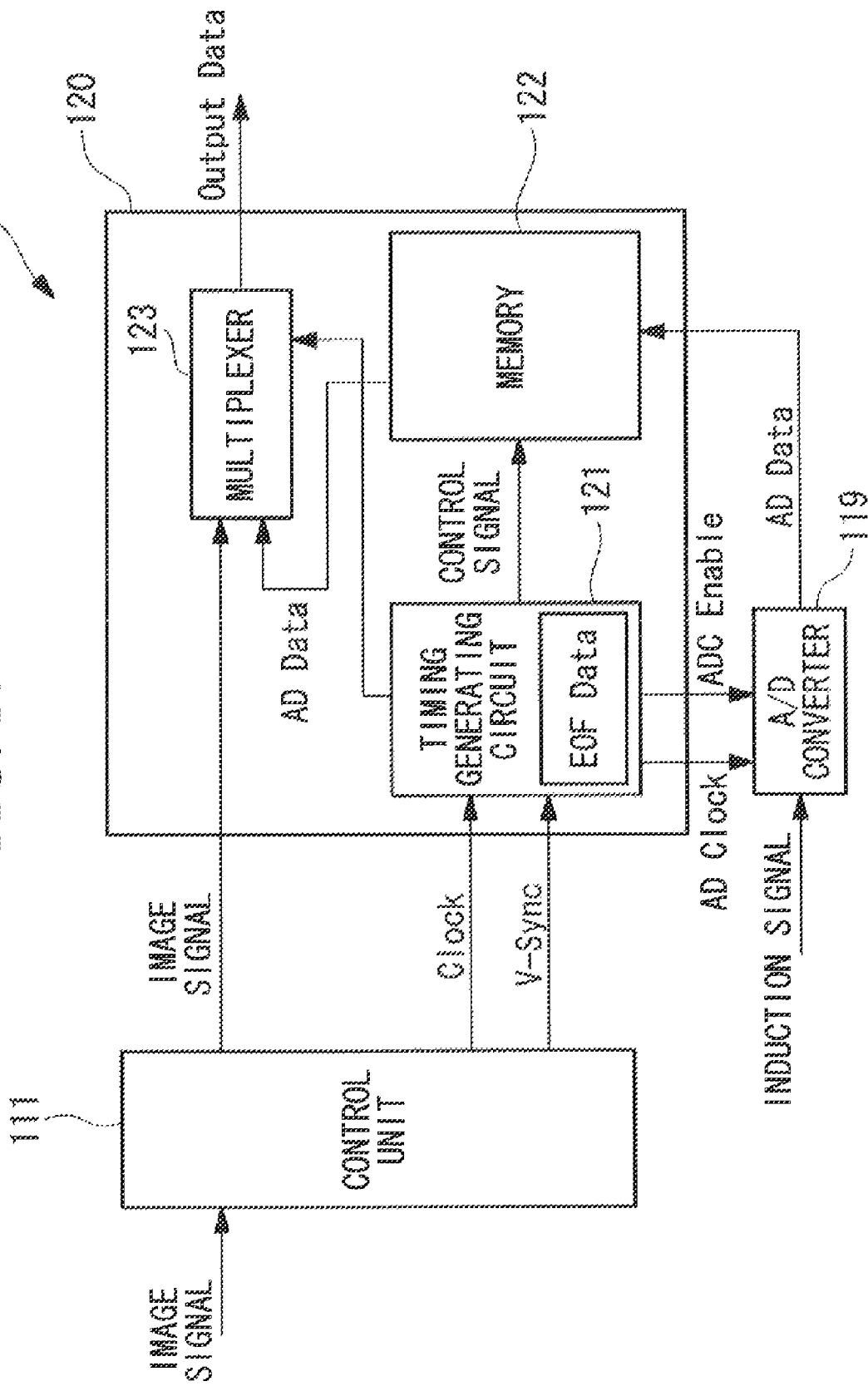
FIG. 17 is a block diagram of an induction-signal processing unit mounted inside the capsule medical device shown in FIG. 15.

More specifically, as shown in FIG. 17, the A/D converter control unit 120 includes a timing generating circuit 121 that is connected to the control unit 111 and generates a timing signal on the basis of a clock signal Clock received from the control unit 111 and a sync signal (for example, a vertical sync signal V-Sync or a horizontal sync signal H-Sync) obtained from the image signal input to the control unit 111; a memory 122 for storing the digital induction-signal output from the A/D converter 119; and a multiplexer 123 that is connected to the memory 122, the timing generating circuit 121, and the control unit 111 and that switches the output of the image signal from the control unit 111 and the position-detection signal from the memory 122 based on the timing signal from the timing generating circuit 121. The timing generating circuit 121 outputs a clock signal Clock and an A/D conversion enable signal to the A/D converter 119. In this way, the A/D converter 119 periodically repeats operation and operation stoppage in synchronization with the operation of the image sensor 115. In this embodiment, the A/D converter 119 operates in a period different from the operation period of the image sensor 115 and the LEDs 117.

The control unit 111 is electrically connected to a battery (power supply) 125 via substrates 114a to 114d and flexible substrates 124a and 124b, is electrically connected to the image sensor 115 via the substrate 114a, and is electrically connected to the LEDs 117 via the flexible substrate 124a and the support member 118. The control unit 111 outputs the image signal acquired by the image sensor 115 to the A/D converter control unit 120 and turns on or off the image sensor 115 and the LEDs 117. In this way, the image sensor 115 and the LEDs 117 are controlled to operate periodically.

The control unit 111 controls the wireless transmitter 110 to transmit the signal output from the multiplexer 123 of the A/D converter control unit 120 to the outside.

In other words, the wireless transmitter 110, for example, transmits data containing a sequence of image signals and induction signals, having predetermined lengths, to the outside.

The permanent magnet 112 is disposed at the rear end section 104c side of the wireless transmitter 110. The permanent magnet 112 is disposed or magnetized such that the magnetization direction (magnetic pole) is orthogonal (for example, the vertical direction in FIG. 16) to the longitudinal axis R. Switch units 126, which are disposed on the substrate 114c, are provided at the forward end section 104b side of the permanent magnet 112. Each switch unit 126 includes an infrared sensor 126a, is electrically connected to the power supply 106, and is electrically connected to the battery 125 via the substrate 114c and the flexible substrate 124a.

The plurality of switch units 126 are arranged in the circumferential direction around the longitudinal axis R and are disposed such that the infrared sensors 126a face outwards in the diameter direction. In this embodiment, a case in which four switch units 126 are provided is described. However, the number of switch units 126 is not limited to four, and, instead, any number of switch units 126 may be provided.

The battery 125 is disposed between the substrates 114b and 114c on the forward end section 104b side of the switch units 126.

The coil 107 is wound inward in the radial direction of the capsule body 104a of the case 104 to form a cylinder. In the drawings, reference number 127 represents a core member (magnetic core) composed of ferrite formed into a cylinder having a center axis that is substantially aligned with the longitudinal axis R.

In this way, the opening direction of the coil 107 is a direction orthogonal to the magnetization direction of the permanent magnet 112. As a result, the magnetic field generated by the permanent magnet 112 is prevented from passing through the inner section of the coil 107, and thus, the magnetic field generated by the permanent magnet 112 does not affect the induction signal generated at the coil 107.

Figure 18:
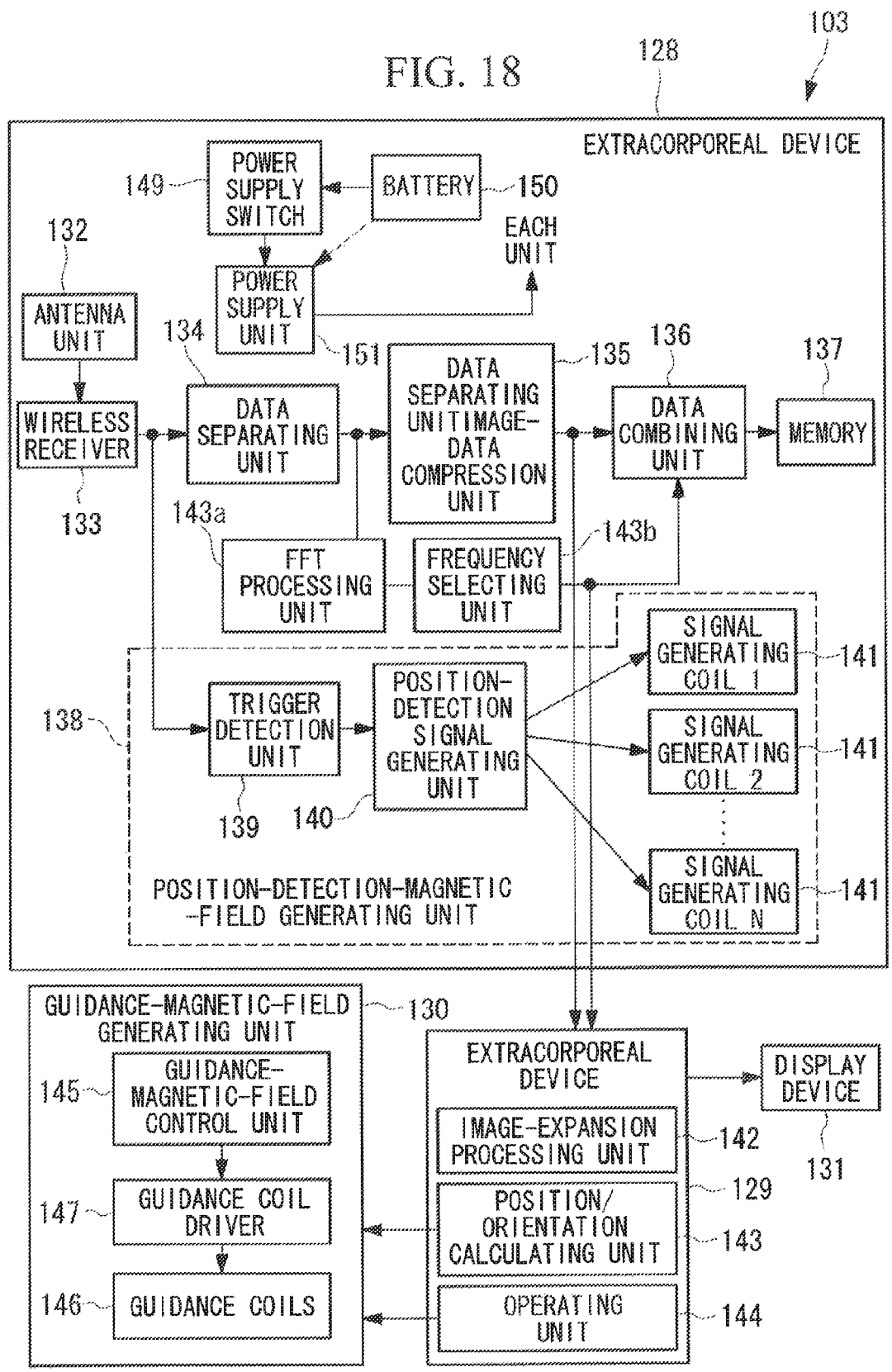
FIG. 18 is a block diagram of an external apparatus of the capsule medical device system shown in FIG. 13.

As shown in FIGS. 14 and 18, the external apparatus 103 includes an extracorporeal device 128 that receives a signal from the capsule medical device 101 and generates a position-detection magnetic field $M_2$; an external control unit 129 that generates an image on the basis of the signal received from the extracorporeal device 128 and calculates the position and orientation of the capsule medical device 101; a guidance-magnetic-field generating unit 130 that generates the guidance magnetic field $M_1$ on the basis of the information of the position and orientation of the capsule medical device 101 output from the external control unit 129; and a display device 131 that displays an image on the basis of an image signal output from the external control unit 129.

The extracorporeal device 128 includes a wireless receiver 133 that receives the image signal and the induction signal from the capsule medical device 101 via an antenna unit 132; a data separating unit 134 that separates the received signal into an image signal and an induction signal; an image-data compression unit 135 that compresses the separated image signal; a data combining unit 136 that combines the compressed image signal and the separated induction signal; a memory 137 that stores the combined data; and a position-detection-magnetic-field generating unit 138 that generates the position-detection magnetic field $M_2$ on the basis of the signal received by the wireless receiver 133.

The signal received by the wireless receiver 133 includes the image signal and the induction signal. Since the image signal has a predetermined length, the data separating unit 134 can easily separate the image signal and the subsequent induction signal.

The position-detection-magnetic-field generating unit 138 includes a trigger detection unit 139 (sync-signal extracting device) that detects a trigger signal, e.g., a vertical sync signal V-Sync or a horizontal sync signal H-Sync, included in the image information; a position-detection signal generating unit (synchronization device) 140 that outputs the position-detection signal at a timing based on the detected trigger signal; and a plurality of signal generating coils 141 that generates the position-detection magnetic field $M_2$ on the basis of the signal output from the position-detection signal generating unit 140.

The external control unit 129 includes an image-expansion processing unit 142 that expands the compressed image signal sent from the extracorporeal device 128 and outputs it to the display device 131; a position/orientation calculating unit (position/orientation data processing unit) 143 that calculates the position and orientation of the capsule medical device 101 on the basis of the induction signal from the extracorporeal device 128 and outputs these to the display device 131; and an operating unit 144 that allows the operator to instruct the traveling direction and/or traveling speed of the capsule medical device 101 on the basis of the image of the inside of the body cavity displayed on the display device 131 and the position and orientation of the capsule medical device 101.

An FFT processing unit 143a that performs Fourier transformation of the received induction signal and a frequency selecting unit 143b that extracts a specific frequency signal having a frequency substantially the same as the frequency of the position-detection magnetic field $M_2$ on the basis of the process result of FFT processing unit 143a generated by the position-detection signal generating unit 140 from induction signal, are provided at a stage before the position/orientation calculating unit 143. The position/orientation calculating unit 143 calculates at least one of the position and orientation of the capsule medical device 101 on the basis of the specific frequency signal extracted in this way. In this embodiment, a specific frequency signal is extracted using FFT. However, a specific frequency can be extracted in the same way using a digital filter circuit, instead of FFT. Similarly, signal processing methods such as wavelet conversion may be selected instead of FFT processing.

The guidance-magnetic-field generating unit 130 includes a guidance-magnetic-field control unit 145 that generates a control signal for the guidance magnetic field $M_1$ on the basis of the operation instruction signal output from the external control unit 129 by the operator and information such as the position and orientation of the capsule medical device 101; a plurality of guidance coils 146 that generates the guidance magnetic field $M_1$ on the basis of the control signal from the guidance-magnetic-field control unit 145; and a guidance coil driver 147 that supplies electric currents to the guidance coils 146.

Here, the operation of the filter 108 described above will be described.

The guidance magnetic field $M_1$ generated at the guidance-magnetic-field generating unit 130 is, for example, an intense magnetic field of 1 mT to 1 T. The generation direction and the magnetic field intensity of the guidance magnetic field $M_1$ are changed at a frequency of 100 Hz or less in order to control the position and orientation of the capsule medical device 101.

Alternatively, the position-detection magnetic field $M_2$ has a magnetic field intensity of approximately 0.01 μT to 100 μT and a frequency of several to several hundred kHz at the position of the capsule medical device 101.

When the direction of the capsule medical device 101 is to be changed by the guidance magnetic field $M_1$, a magnetic torque is generated by forming an angle between the magnetization direction of the permanent magnet 112 inside the capsule medical device 101 and the direction of the guidance magnetic field $M_1$. The magnetic torque is maximized when the angle between the magnetization direction of the permanent magnet 112 and the direction of the guidance magnetic field $M_1$ is 90°.

The coil 107 inside the capsule medical device 101 generates an induction (voltage) signal upon receiving the magnetic field. If the induction signal is represented by V, then $$V = 2\pi f B S N \cos \theta$$

Here, f represents the frequency of the magnetic field, B represents the intensity of the magnetic field, S represents the cross-sectional area of the coil, N represents the winding turns of the coil 107, and θ represents the angle between the direction of the magnetic field and the opening direction of the coil 107.

For example, when the induction signal V generated at the coil 107 is determined, where the intensity and frequency of the guidance magnetic field $M_1$ are 100 mT and 10 Hz, respectively, the intensity and frequency of the position-detection magnetic field $M_2$ are 1 μT and 10 kHz, respectively, the angle between the opening direction of the coil 107 and the direction of the magnetic field is 60°, the cross-sectional area of the coil 107 is $10 \times 10^{-6}$ m², and the number of windings of the coil 107 is 400, the induction signal intensity due to the guidance magnetic field $M_1$ is approximately 100 mV, and the induction signal intensity due to the position-detection magnetic field $M_2$ is approximately 2 mV.

The signal detected in this state is illustrated in FIG. 7.

If this signal is directly A/D converted, a large portion of the dynamic range of the A/D converter 119 is used for the induction signal generated by the guidance magnetic field $M_1$, and thus, the induction signal generated by the position-detection magnetic field $M_2$ cannot be detected with good precision.

According to this embodiment, by connecting the high-pass filter 108, having a cutoff frequency of approximately 1 kHz, to the coil 107, the induction signal at a frequency of 10 Hz in the guidance magnetic field $M_1$ can be attenuated by −40 dB. In this way, as shown in FIG. 8, the induction signal generated by the guidance magnetic field $M_1$ is attenuated to approximately 1 mV, and the induction signal generated by the position-detection magnetic field $M_2$ is passed at approximately 2 mV. By connecting the filter 108 to the coil 107 in this way, the effect of the guidance magnetic field $M_1$ is reduced, and the induction signal generated by the position-detection magnetic field $M_2$ can be detected with good precision.

The operation of the capsule medical device 101 and the capsule medical device system 102 according to this embodiment, having the above-described configuration, will be described below.

To acquire an image of the inside of the body cavity of the subject using the capsule medical device system 102 according to this embodiment, the subject is disposed in a space S where the guidance magnetic field $M_1$ due to the guidance coils 146, which are disposed as shown in FIG. 13, acts.

Next, the infrared sensor 126a of the capsule medical device 101 is irradiated with infrared rays generated by an infrared generating device, which is not shown in the drawings, to supply power to the capsule medical device 101. Then, the capsule medical device 101 is introduced via the mouth or anus of the subject. In the external apparatus 103, electric power is supplied to each unit by operating a power supply switch 149 of the extracorporeal device 128 with a battery 150 and switching a power supply unit 151 to an ON state.

In the capsule medical device 101 introduced into the body cavity, operation of the image-acquisition unit 105 is started after a predetermined amount of time, and an image of the inner surface of the body cavity illuminated by illumination light from the LEDs 117 is acquired by the image sensor 115. The acquired image signal is sent to the A/D converter control unit 120 via the control unit 111 is further sent to the wireless transmitter 110 at a timing set by the timing generating circuit 121 on the basis of the clock signal Clock and the trigger signal (for example, the vertical sync signal V-Sync) generated at the control unit 111, and is transmitted outside the body via the wireless transmitter 110.

The transmitted image signal is received by the wireless receiver 133 via the antenna unit 132 provided in the extracorporeal device 128. The received image signal is input to the position-detection-magnetic-field generating unit 138, and the trigger signal, such as the vertical sync signal V-Sync, is detected. Then, the position-detection signal generating unit 140 is started up on the basis of the detected trigger signal, the signal generating coils 141 are energized, and the position-detection magnetic field $M_2$ is generated in the space S where the subject is disposed.

When the generated position-detection magnetic field $M_2$ acts upon the capsule medical device 101, an induction signal is induced at the coil 107 by the position-detection magnetic field $M_2$ passing through the inside of the coil 107 in the capsule medical device 101. The induction signal is input to the position-detection-signal processing unit 109 via the filter 108, is A/D converted at a timing set by the timing generating circuit 121, and is stored in the memory 122. Then, the induction signal is sent to the wireless transmitter 110 via the multiplexer (represented as MUX in the drawings) 123, which is switched at a timing set by the timing generating circuit 121, and is transmitted outside the body via the wireless transmitter 110.

The transmitted induction-signal is received by the wireless receiver 133 via the antenna unit 132 provided in the extracorporeal device 128. The received induction signal is separated from the image signal by the data separating unit 134. The separated induction signal is directly sent to the external control unit 129, and the image signal is sent to the external control unit 129 after being compressed at the image-data compression unit 135. The induction signal and the compressed image signal are combined in a mutually linked form at the combining unit 136 and are stored in the memory 137.

The image signal sent to the external control unit 129 is expanded at the image-expansion processing unit 142 and is sent to the display device 131 for display. The induction signal sent to the external control unit 129 is sent to the position/orientation calculating unit 143 via the FFT processing unit 143a and the frequency selecting unit 143b and is used for calculating the position and orientation of the capsule medical device 101. The calculated position and orientation of the capsule medical device 101 are sent to the display device 131 for display and are also sent to the guidance-magnetic-field generating unit 130 for calculating the guidance magnetic field $M_1$ to be generated.

After confirming the image of the inner surface of the body cavity and the information of the position and the orientation of the capsule medical device 101 displayed on the display device 131, the operator operates the operating unit 144 of the external control unit 129 in order to input the traveling direction and the traveling speed of the capsule medical device 101 to the guidance-magnetic-field generating unit 130. The guidance-magnetic-field generating unit 130 operates the guidance coil driver 147 such that the intensity and direction of the guidance magnetic field $M_1$ to be generated are achieved on the basis of the instruction signal for the traveling direction and traveling speed input from the operating unit 144 and the information of the position and orientation of the capsule medical device 101 input from the position/orientation calculating unit 143. In this way, the guidance coils 146 are energized, and a desired guidance magnetic field $M_1$ is generated in the space S where the subject is disposed.

When the guidance magnetic field $M_1$ acts upon the capsule medical device 101, the permanent magnet 112 disposed inside the capsule medical device 101 generates a driving force for rotating the capsule medical device 101 to match the magnetization direction to the direction of the guidance magnetic field $M_1$. When the guidance magnetic field $M_1$ is generated in a direction at an angle to the longitudinal axis R of the capsule medical device 101 with respect to the magnetization direction of the permanent magnet 112, a driving force for changing the orientation of the capsule medical device 101 is generated. On the other hand, when the driving force is generated at an angle to the circumferential direction of the capsule medical device 101 with respect to the magnetization direction of the permanent magnet 112, a driving force for rotating the capsule medical device 101 around the longitudinal axis R is generated.

Since the helical section 113 is provided on the outer circumferential surface of the case of the capsule medical device 101, a propulsion force is generated in the direction of the longitudinal axis R by the helical section 113 when the capsule medical device 101 rotates around the longitudinal axis R due to the driving force. In this way, the capsule medical device 101 is propelled in the direction of the longitudinal axis R.

In this case, the coil 107 disposed in the capsule medical device 101 receives both the guidance magnetic field $M_1$ and the position-detection magnetic field $M_2$ and generates induction signals corresponding to the intensity etc. of the guidance magnetic field $M_1$ and position-detection magnetic field $M_2$. However, in the capsule medical device 101 and the capsule medical device system 102 according to this embodiment, since the filter 108 is connected to the coil 107, the induction signal due to the guidance magnetic field $M_1$ is A/D converted in an attenuated state and is transmitted to the external apparatus 103. Therefore, at the external apparatus 103, as described above, the effect of the guidance magnetic field $M_1$ can be reduced, and the position-detection signal generated by the position-detection magnetic field $M_2$ can be detected with good precision.

Accordingly, since the position and orientation of the capsule medical device 101 are calculated with good precision by using the induction signal for position detection detected with precision in this way, the guidance-magnetic-field control unit 145 can drive the guidance coil driver 147 so as to generate the guidance magnetic field $M_1$ accurately corresponding to the instructions from the operator. As a result, there is an advantage in that the capsule medical device 101 can be guided with good precision, and an image of a desired site inside the body cavity can be acquired.

With the capsule medical device system 102 according to this embodiment, since the capsule medical device 101 and the external apparatus 103 are operated in synchronization at a timing generated on the basis of the vertical sync signal V-Sync or the horizontal sync signal H-Sync extracted from the image signal, the capsule medical device 101 can perform A/D conversion on the induction signal from the coil 107 only when the position-detection magnetic field $M_2$ is generated by the extracorporeal device 128. Therefore, the processing of the induction-signal by the induction-signal processing unit 109 can be stopped while the position-detection magnetic field $M_2$ is not generated, and thus, power can be conserved.

Figure 19:
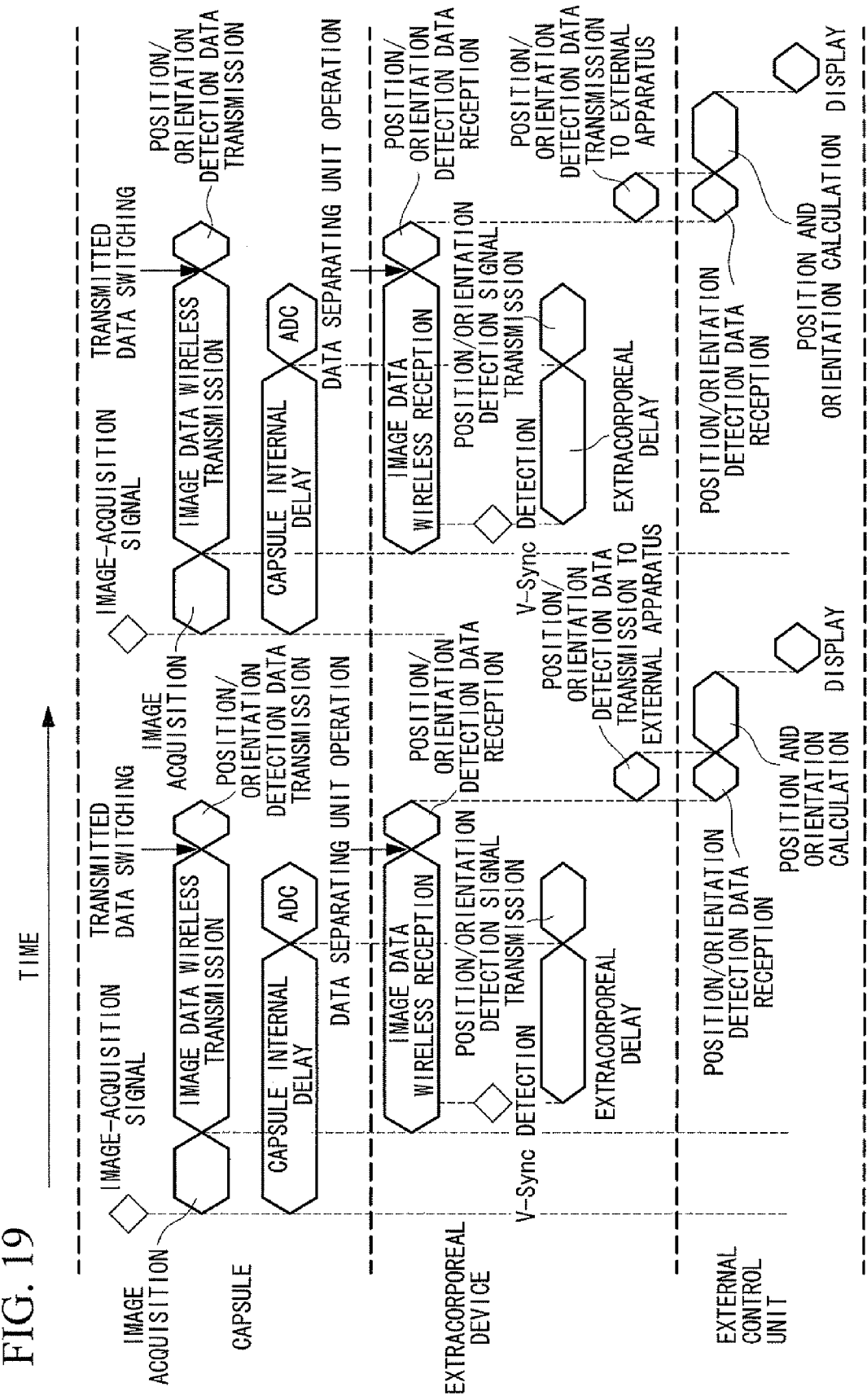
FIG. 19 is a timing chart illustrating the operation timing of the capsule medical device system according to the third embodiment.

More specifically, as shown in FIG. 19, the control unit 111 of the capsule medical device 101 operates the A/D converter 119 after a predetermined delay time (capsule internal delay) from when image acquisition by the image-acquisition unit 105 is started, and then stops the A/D converter 119 upon completion of the processing. The capsule internal delay is set such that the processing of the A/D converter 119 is completed between the start point of image acquisition by the image-acquisition unit 105 and the completion of wireless transmission of the image data. In this way, upon completion of the wireless transmission of the image data, the position/orientation detection data can be transmitted, and the operating time of the wireless transmitter 110 can be minimized, thus reducing power consumption.

Subsequently, this operation is repeated each time image acquisition is performed by the image-acquisition unit 105.

In this way, the capsule medical device 101 operates the A/D converter 119 for only a minimum required time, and thus, power consumption is reduced.

In the external apparatus 103, the position-detection-magnetic-field generating unit 138 generates the position-detection magnetic field $M_2$ after a predetermined delay time (extracorporeal delay) from the moment when a sync signal contained in the signal received by the wireless receiver 133 is detected by the trigger detection unit 139. By taking into consideration the time lag from the moment the wireless transmitter 110 generates the sync signal to the moment the sync signal is detected by the trigger detection unit 139, this extracorporeal delay is set such that the period the position-detection-magnetic-field generating unit 138 is generating the position-detection magnetic field $M_2$ overlaps with the period the A/D converter 119 is operating.

Subsequently, this operation is repeated every time image acquisition is performed by the image-acquisition unit 105.

In this way, the external apparatus 103 operates the position-detection-magnetic-field generating unit 138 for only a minimum required time, and thus, power consumption is reduced. Since the signal receiving device Re can be operated when signal information, such as the phase of the position-detection magnetic field $M_2$ generated at the position-detection-magnetic-field generating unit 138, is known in advance, the operating time can be minimized, and thus, power consumption can be reduced.

In this embodiment, since a signal that is contained in the image signal output from the image-acquisition unit 105 is used as the sync signal, the capsule medical device 101 according to the present invention can be provided by slightly modifying a conventional capsule medical device.

In the capsule medical device 101, since the A/D converter 119 is constructed to operate during a period different from the operation period of the image-acquisition unit 105, a decrease in the voltage supplied to the power supply 106 of the capsule medical device 101 when these devices are operated can be suppressed, and the adverse effect of a reduction in the voltage supplied to the devices mounted in the capsule medical device 101 can be reduced.

In the capsule medical device system 102, the signal received by the wireless reception device of the external apparatus 103 is processed by the FFT processing unit 143a, and the frequency selecting unit 143b extracts the frequency component corresponding to the position-detection signal from the processing result.

The signal transmitted from the wireless transmission device of the capsule medical device (a signal containing a plurality of position-detection signals received by the signal receiving device Re) is extracted from the signal received by the wireless reception device of the external apparatus 103, and unwanted components, such as noise, are removed.

In this way, the amount of data processing by the position/orientation calculating unit 143 is reduced. Since only minimum information required for calculating the position and orientation of the capsule medical device 101 needs to be stored in the memory 137, where the signal received by the wireless receiver 133 is stored, the storage capacity of the memory 138 can be reduced. Since complex frequency selection processing does not have to be performed by the signal processing circuit of the signal receiving device Re inside the capsule medical device 101, power consumption of the capsule medical device 101 can be reduced.

In this embodiment, the capsule medical device 101 and the external apparatus 103 are synchronized by timing generated on the basis of the vertical sync signal V-Sync extracted from the image signal. However, it is not limited thereto, and synchronization may be carried out by timing generated on the basis of other trigger signals, such as the horizontal sync signal extracted from the image signal.

For example, when the capsule medical device 101 has a data compressing device that compresses the image information acquired by the image-acquisition unit 105 and generates a compressed image signal, the vertical sync signal of the image signal and the horizontal sync signal of the image signal are compressed, and these sync signals cannot be directly detected from the compressed image signal. In such a case, data that specifies the position of the compressed data signal (for example, a header data block of the compressed image signal) may be detected and used as a sync signal.

When a data compressing device is provided in the capsule medical device 101, the image-data compression unit 135 of the external apparatus 103 is omitted.

In this embodiment, a high-pass filter having a cutoff frequency of 1 kHz is used as the filter 108. Instead, however, a band-pass filter may be used.

Furthermore, in this embodiment, a capsule medical device system that guides the capsule medical device 101, having the permanent magnet 112 embedded therein, by an external magnetic field has been described. However, the present invention is not limited thereto, and the same results can be achieved by using a capsule medical device that is orally introduced into the subject's body cavity, travels through the subject's digestive tract by peristaltic movement of the digestive tract, and acquires bio information in the body cavity while traveling, or by using a capsule medical device that indwells inside the body cavity.

The invention claimed is:

1. A capsule medical device comprising:
   a bio-information detecting device configured to detect bio information of the inside of a body cavity;
   a magnet configured to generate a driving force by a guidance magnetic field applied from outside the body;
   a coil configured to receive a position-detection magnetic field applied from outside the body and to generate a position-detection signal;
   a filter device, connected to the coil, configured to attenuate an induction signal component due to the guidance magnetic field incident on the coil; and
   a wireless transmission device configured to externally transmit the position-detection signal which has passed through the filter device and the bio information which has been detected by the bio-information detecting device,
   wherein the coil comprises two or more coils, and opening directions of the coils differ,
   the opening directions of the two or more coils and a direction of a magnetic field formed by the magnet at the position of the coil are substantially orthogonal, and
   each of the two or more coils has a center axis that is substantially aligned with a longitudinal axis of the capsule medical device, and is disposed such that the opening directions are inclined with respect to the longitudinal axis of the capsule medical device.

2. The capsule medical device according to claim 1, wherein the two or more coils are disposed at the same position.

3. The capsule medical device according to claim 1,
   wherein identification information required for detecting at least one of position and orientation by using the position-detection signal is stored, and
   wherein the wireless transmission device externally transmits the identification information.

4. The capsule medical device according to claim 3, wherein the identification information includes relative positions of the coils and relative angles of the opening directions.

5. The capsule medical device according to claim 3, wherein the identification information includes relative positions and relative angles of the coils, relative positions of the coils and the magnet, and relative angles of the opening directions of the coils and a magnetization direction of the magnet.

6. The capsule medical device according to claim 1, further comprising:
   a switching device configured to switch connections between the two or more coils and the filter device.

7. The capsule medical device according to claim 6, wherein the switching device and the bio-information detecting device are operated in synchronization.

8. The capsule medical device according to claim 1, further comprising:
   a position-detection signal processing device configured to process the position-detection signal, which has passed through the filter device, and input it to the wireless transmission device, and wherein the position-detection signal processing device and the bio-information detecting device are operated in synchronization.

9. A capsule medical device system comprising:
a capsule medical device according to claim 3; and
an external apparatus disposed outside a body,
wherein the external apparatus includes,
a wireless reception device configured to receive a signal transmitted from the wireless transmission device,
an information extracting device configured to extract the position-detection signal and the identification information from the signal received by the wireless reception device,
a position/orientation calculating device configured to calculate a position and an orientation of the capsule medical device and a magnetization direction of the magnet on the basis of the position-detection signal and the identification information extracted by the information extracting device,
a guidance-magnetic-field generating device configured to generate a guidance magnetic field, and
a position-detection-magnetic-field generating device configured to generate the position-detection magnetic field.

10. A capsule medical device system comprising:
a capsule medical device according to claim 1; and
an external apparatus disposed outside a body,
wherein the external apparatus includes,
a wireless reception device configured to receive a signal transmitted from the wireless transmission device,
a position-detection signal extracting device configured to extract the position-detection signal from the signal received by the wireless reception device,
a position/orientation calculating device configured to calculate at least one of position and orientation of the capsule medical device on the basis of the position-detection signal extracted by the position-detection signal extracting device,
a guidance-magnetic-field generating device configured to generate a guidance magnetic field, and
a position-detection-magnetic-field generating device configured to generate the position-detection magnetic field.

11. The capsule medical device system according to claim 10, wherein the position/orientation calculating device processes the position-detection signal extracted by the position-detection signal extracting device, extracts a specific frequency signal having a frequency substantially the same as the frequency of the position-detection magnetic field which is generated by the position-detection signal generating device, and calculates at least one of the position and orientation of the capsule medical device on the basis of the extracted specific frequency signal.

12. A capsule medical device system comprising:
a capsule medical device according to claim 1; and
an external apparatus disposed outside a body,
wherein the external apparatus includes,
a wireless reception device configured to receive a signal transmitted from the wireless transmission device,
an information extracting device configured to extract the position-detection signal from the signal received by the wireless reception device,
an identification-information storing device configured to store identification information including relative positions and relative angles of opening directions of two or more coils of the capsule medical device,
a position/orientation calculating device configured to calculate a position and an orientation of the capsule medical device and a magnetization direction of the magnet on the basis of the identification information read out from the identification-information storing device and the position-detection signal extracted by the information extracting device,
a guidance-magnetic-field generating device configured to generate a guidance magnetic field, and
a position-detection-magnetic-field generating device configured to generate the position-detection magnetic field.

13. The capsule medical device system according to claim 12, wherein the guidance-magnetic-field generating device is controlled on the basis of a position and the orientation of the capsule medical device and the magnetization direction of the magnet calculated by the position/orientation calculating device.

14. A capsule medical device comprising:
a bio-information detecting device configured to be introduced into a subject to detect bio information of the subject;
a magnet configured to generate a driving force by a guidance magnetic field applied from outside the subject;
a coil configured to receive a position-detection magnetic field applied from outside the subject and for generating a position-detection signal;
a filter device, connected to the coil, configured to attenuate an induction signal component due to the guidance magnetic field incident on the coil; and
a wireless transmission device configured to externally transmit the position-detection signal which has passed through the filter device and the bio information detected by the bio-information detecting device,
wherein the coil comprises two or more coils, and opening directions of the coils differ, the opening directions of the two or more coils and a direction of a magnetic field formed by the magnet at the position of the coil are substantially orthogonal, and each of the two or more coils has a center axis that is substantially aligned with the longitudinal axis of the capsule medical device, and is disposed such that the opening directions are inclined with respect to the longitudinal axis of the capsule medical device,
wherein the capsule medical device includes a signal receiving device configured to perform reception operation of the position-detection signal in synchronization with an operation of the bio-information detecting device, and
wherein the wireless transmission device transmits the bio information detected by the bio-information detecting device, information of the position-detection signal received by the signal receiving device, and a sync signal which is synchronized with the operation of the signal receiving device.

15. The capsule medical device according to claim 14,
wherein the bio-information detecting device periodically detects the bio information of the subject, and
wherein the signal receiving device repeats a reception operation and operation stoppage in synchronization with the operation of the bio-information detecting device.

16. The capsule medical device according to claim 14,
wherein the bio-information detecting device is an image-acquisition unit for acquiring an image of the inside of the subject and for outputting an image signal, and wherein the sync signal is a signal included, in advance, in the image signal output from the image-acquisition unit.

17. The capsule medical device according to claim 16, wherein the sync signal is a vertical sync signal of the image signal.

18. The capsule medical device according to claim 16, wherein the sync signal is a horizontal sync signal of the image signal.

19. The capsule medical device according to claim 14, wherein the signal receiving device operates in a period different from an operation period of the bio-information detecting device.

20. A capsule medical device system comprising:
a capsule medical device, according to claim 14, introduced into a subject, and configured to acquires bio information of the subject, and wirelessly transmits the bio information; and
an external apparatus provided outside the subject configured to receive the bio information generated by the capsule medical device,
wherein the external apparatus includes,
a position-detection signal generating device configured to wirelessly transmit a position-detection signal,
a wireless reception device configured to receive a signal generated by the wireless transmission device of the capsule medical device,
a sync-signal extracting device configured to extract the sync signal from the signal received by the wireless reception device, and
a synchronization device configured to synchronize a generation timing of the position-detection signal of the position-detection signal generating device and the operation timing of the signal receiving device of the capsule medical device on the basis of the sync signal extracted at the sync-signal extracting device.

21. The capsule medical device system according to claim 20,
wherein the signal receiving device of the capsule medical device is constructed to receive a plurality of the position-detection signals in a plurality of operations carried out at predetermined intervals, and
wherein the external apparatus has a position/orientation calculating device configured to calculate a position or an orientation of the capsule medical device, and the position/orientation calculating device includes
a frequency selecting unit configured to extract a frequency component corresponding to the position-detection signal received by the wireless reception device, and
a position/orientation data processing unit configured to calculate at least one of position and orientation of the capsule medical device on the basis of the frequency component selected by the frequency selecting unit.

22. The capsule medical device system according to claim 21,
wherein the position/orientation calculating device includes an FFT processing unit configured to perform Fourier transformation of the signal received by the wireless reception device, and
wherein the frequency selecting unit receives a processing result from the FFT processing unit and extracts a frequency component corresponding to the position-detection signal.

23. The capsule medical device system according to claim 21,
wherein the external apparatus includes a guidance-magnetic-field generating device configured to generate a guidance magnetic field which acts on the magnet inside the capsule medical device to guide the capsule medical device, and
wherein the filter device included in the signal receiving device of the capsule medical device removes a frequency component contained in the guidance magnetic field.

24. A capsule medical device configured to be introduced into a subject to acquire bio information of the subject and receives a position-detection signal transmitted from an external apparatus provided outside the subject, the capsule medical device comprising:
a bio-information acquiring device configured to acquire bio information of the subject;
a magnet configured to generate a driving force by a guidance magnetic field applied from the external apparatus;
two or more coils configured to receive a position-detection magnetic field applied from the external apparatus and to generate a position-detection signal;
a signal receiving device configured to carry out a reception operation of the position-detection signal in synchronization with an operation of the bio-information acquiring device; and
a wireless transmission device configured to transmit the bio information acquired by the bio-information acquiring device, information of the position-detection signal received by the signal receiving device, and a sync signal which is synchronized with the operation of the signal receiving device,
wherein opening directions of the two or more coils differ,
the opening direction of the coils and a direction of a magnetic field formed by the magnet at the position of the coils are substantially orthogonal, and
each of the two or more coils has a center axis that is substantially aligned with the longitudinal axis of the capsule medical device, and is disposed such that the opening directions are inclined with respect to the longitudinal axis of the capsule medical device.

25. The capsule medical device according to claim 24,
wherein the bio-information acquiring device periodically detects the bio information of the subject, and
wherein the signal receiving device repeats a reception operation and operation stoppage in synchronization with the operation of the bio-information acquiring device.

26. The capsule medical device according to claim 24,
wherein the bio-information acquiring device is an image-acquisition unit configured to acquire an image of the inside of the subject and output an image signal, and
wherein the sync signal is a signal included, in advance, in the image signal output from the image-acquisition unit.

27. The capsule medical device according to claim 26, wherein the sync signal is a vertical sync signal of the image signal.

28. The capsule medical device according to claim 26, wherein the sync signal is a horizontal sync signal of the image signal.

29. The capsule medical device according to claim 24, wherein the signal receiving device operates in a period different from an operation period of the bio-information acquiring device.

30. A capsule medical device system comprising:
a capsule medical device, according to claim 24, that is introduced into a subject, acquires bio information of the subject, and configured to wirelessly transmit the bio information; and an external apparatus for receiving the bio information generated by the capsule medical device, the external apparatus being provided outside the subject, wherein the external apparatus includes, a position-detection signal generating device configured to wirelessly transmit transmitting a position-detection signal, a wireless reception device configured to receive a signal generated by the wireless transmission device of the capsule medical device, a sync-signal extracting device configured to extract the sync signal from the signal received by the wireless reception device, and a synchronization device configured to synchronize a generation timing of the position-detection signal of the position-detection signal generating device and the operation timing of the signal receiving device of the capsule medical device on the basis of the sync signal extracted at the sync-signal extracting device.

31. The capsule medical device system according to claim 30, wherein the signal receiving device of the capsule medical device is constructed to receive a plurality of the position-detection signals in a plurality of operations carried out at predetermined intervals, and wherein the external apparatus has a position/orientation calculating device configured to calculate the position or the orientation of the capsule medical device, and the position/orientation calculating device includes, a frequency selecting unit configured to extract a frequency component corresponding to the position-detection signal received by the wireless reception device, and a position/orientation data processing unit configured to calculate at least one of position and orientation of the capsule medical device on the basis of the frequency component selected by the frequency selecting unit.

32. The capsule medical device system according to claim 31, wherein the position/orientation calculating device includes an FFT processing unit configured to perform Fourier transformation of the signal received by the wireless reception device, and wherein the frequency selecting unit receives a processing result from the FFT processing unit and extracts a frequency component corresponding to the position-detection signal.

33. The capsule medical device system according to claim 31, wherein the capsule medical device has a magnet therein, wherein the external apparatus includes a guidance-magnetic-field generating device configured to generate a guidance magnetic field which acts on the magnet to guide the capsule medical device, and wherein the signal receiving device of the capsule medical device includes a filter device configured to remove a frequency component contained in the guidance magnetic field.

\* \* \* \* \*